(12) United States Patent
Nagata

(10) Patent No.: US 6,287,113 B1
(45) Date of Patent: Sep. 11, 2001

(54) FULL REPRODUCTION ARTICULATOR

(76) Inventor: Kazuhiro Nagata, 9-37, Gakuen-nishi-machi 2-chome, Kodaira-shi, Tokyo 178-0045 (JP)

( * ) Notice: Subject to any disclaimer, the term of this patent is extended or adjusted under 35 U.S.C. 154(b) by 0 days.

(21) Appl. No.: 09/480,769

(22) Filed: Jan. 10, 2000

Related U.S. Application Data

(63) Continuation of application No. PCT/JP98/04764, filed on Oct. 21, 1998, now abandoned.

(30) Foreign Application Priority Data

May 14, 1998 (JP) ................................. 10-131931

(51) Int. Cl.[7] ..................................................... A61C 11/00
(52) U.S. Cl. ..................................................... 433/57
(58) Field of Search ........................................... 433/54–60

(56) References Cited

U.S. PATENT DOCUMENTS

| 4,715,814 | 12/1987 | Kaoru et al. |
| 4,764,113 | * 8/1988 | Hiranuma .............................. 433/56 |
| 5,385,470 | 1/1995 | Polz . |
| 5,632,619 | 5/1997 | Polz . |

* cited by examiner

Primary Examiner—Nicholas D. Lucchesi
(74) Attorney, Agent, or Firm—McCormick, Paulding & Huber LLP

(57) ABSTRACT

A full reproduction articulator faithfully and accurately reproduces jaw movement, particularly the chewing movement, including individual differences. It includes a mandibular model member (10), a base (11) erected on this mandibular model member (10), two condyle balls (12, 12) projecting from this base (11), a maxillary model member (13) that occludes the mandibular model member (10), and condyle boxes (17) linked to both sides of the maxillary model member (13) and in contact with the two condyle balls (12, 12) for regulating movement in the anterior/posterior direction, left/right direction and vertical direction of the maxillary model member (13). A Bennett lift mechanism (16) is also provided on the base (11) for lifting the maxillary model member (13) from the working side condyle ball (12) when the maxillary model member (13) moves in the left/right direction, independently of the working side condyle box (17).

20 Claims, 18 Drawing Sheets

(a)
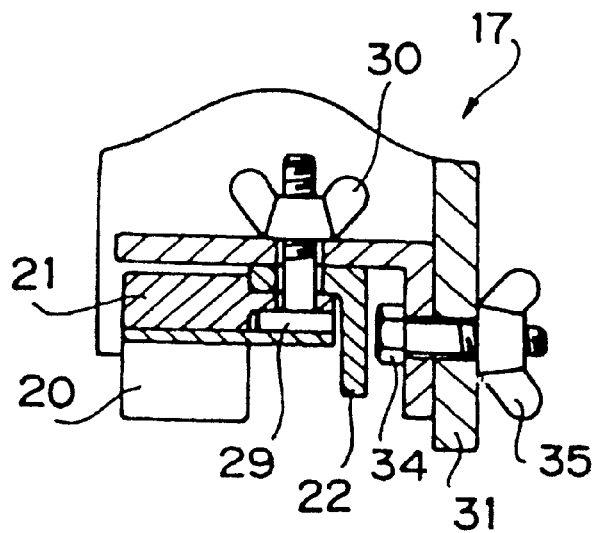
(b)
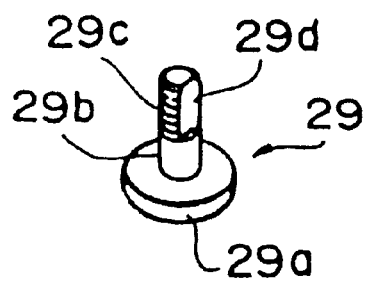
FIG. 3

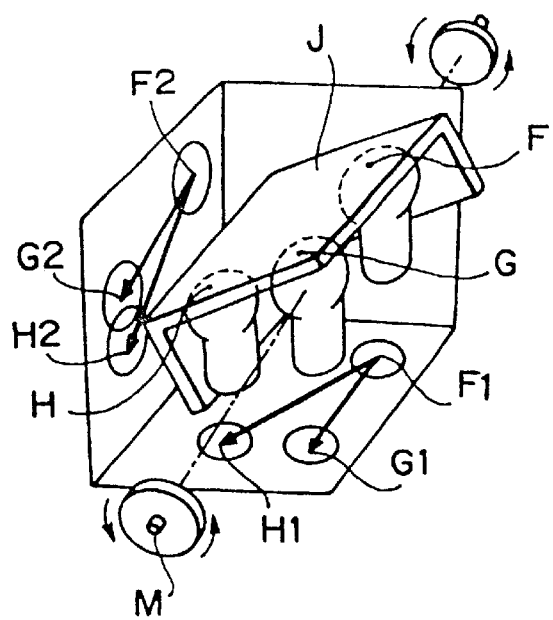
F I G. 6
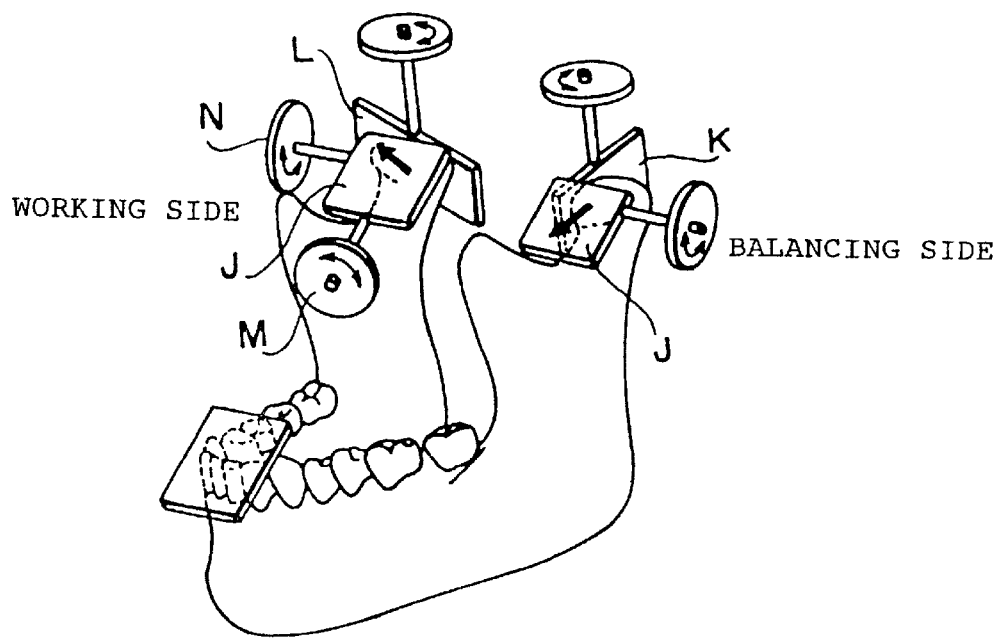
F I G. 7

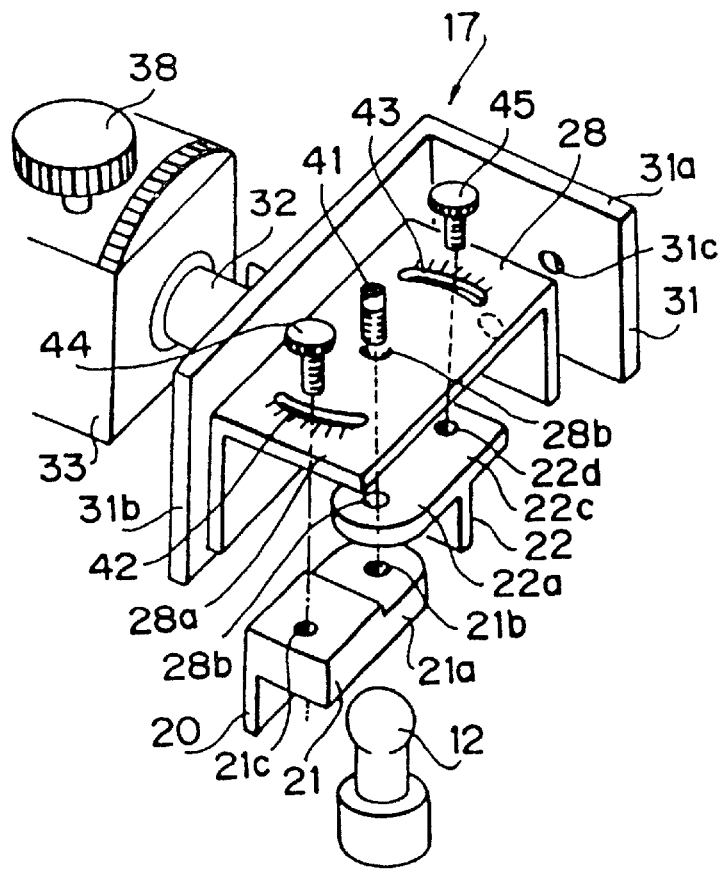
F I G. 8
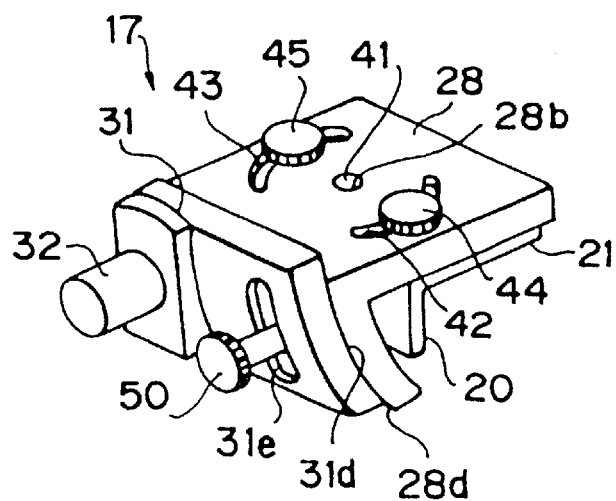
F I G. 9

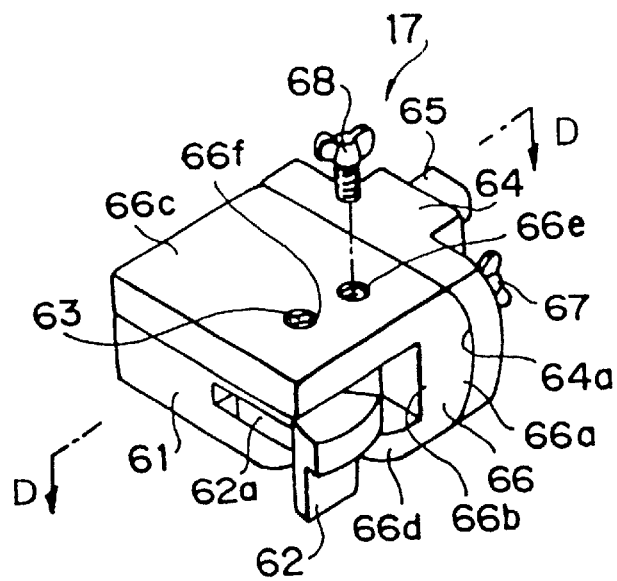
F I G. 1 0
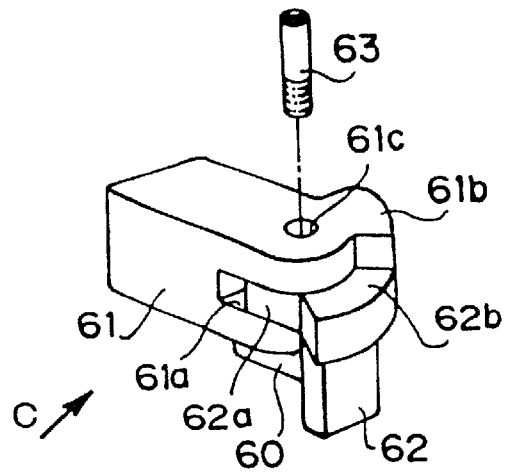
F I G. 1 1
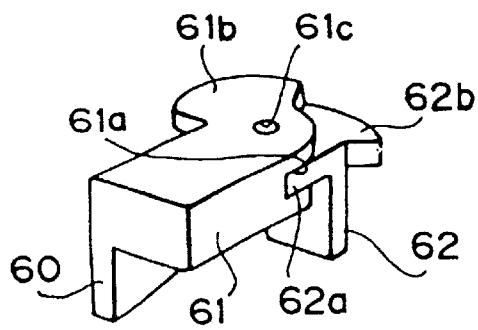
F I G. 1 2

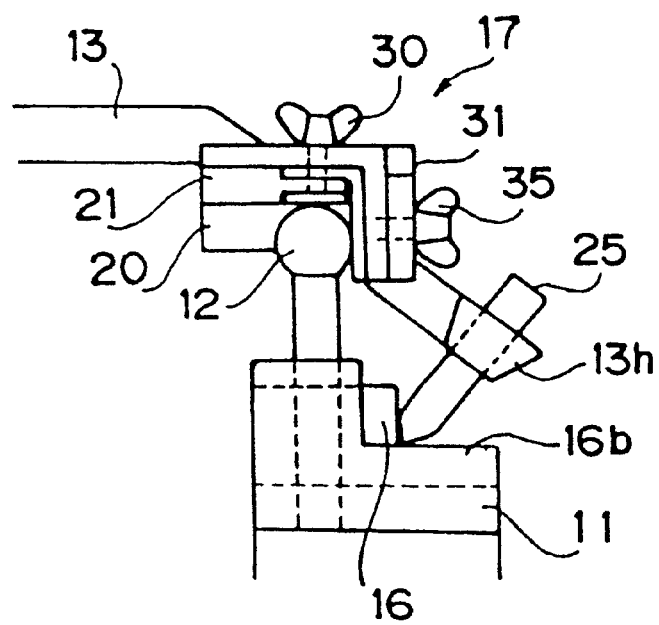
F I G. 1 7
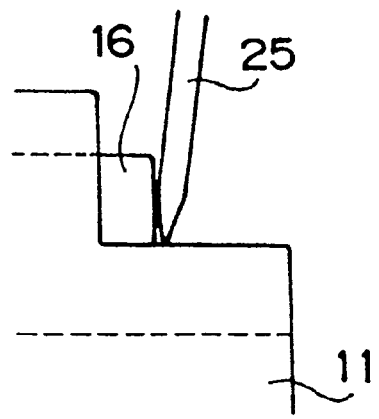
F I G. 1 8

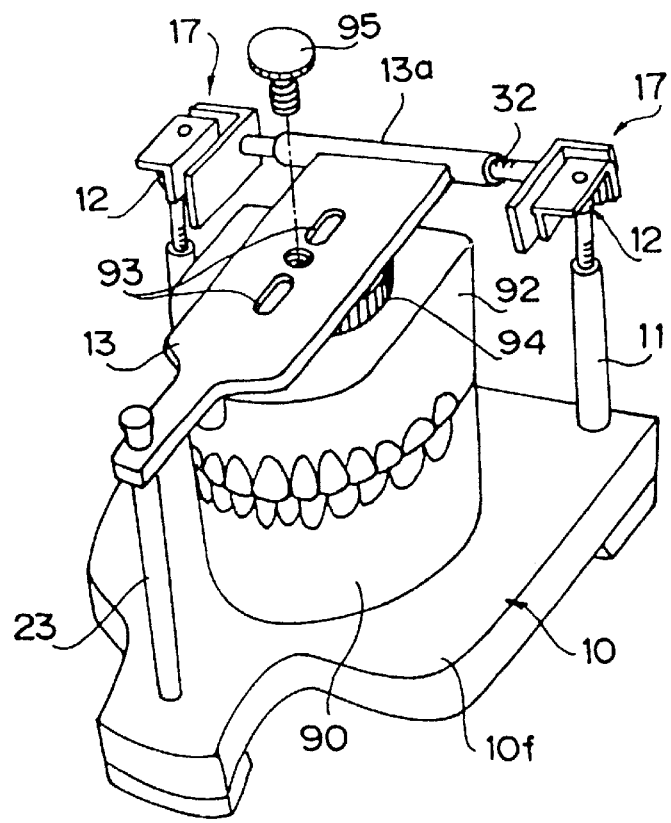
F I G. 2 1
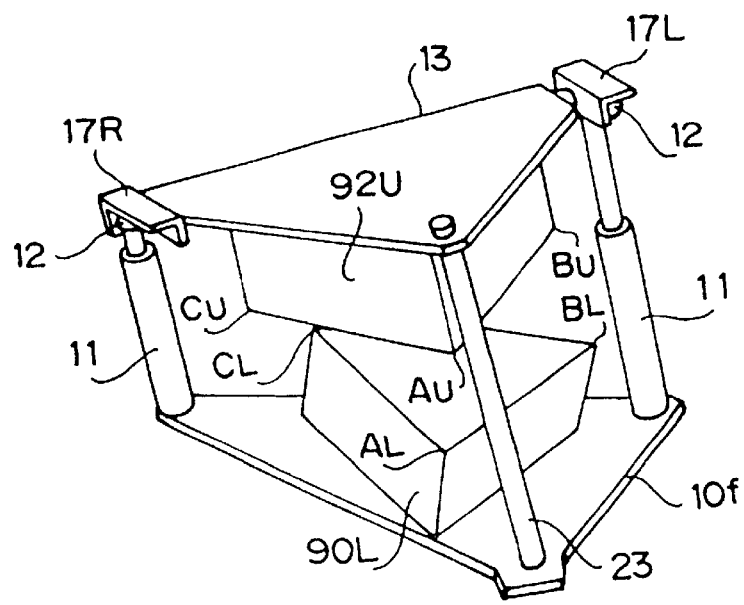
F I G. 2 2

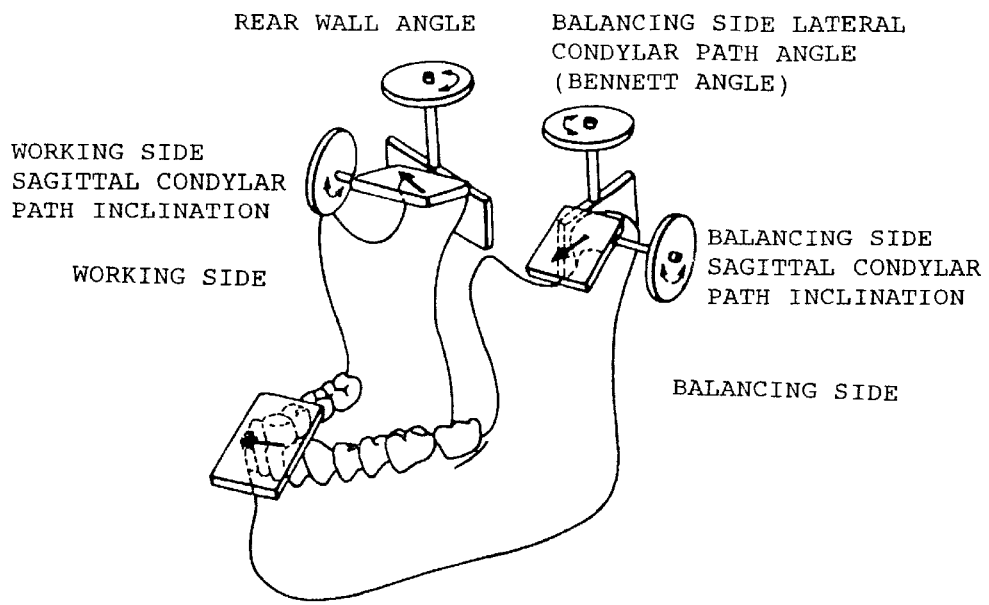
FIG. 32
FIG. 33a
FIG. 33b
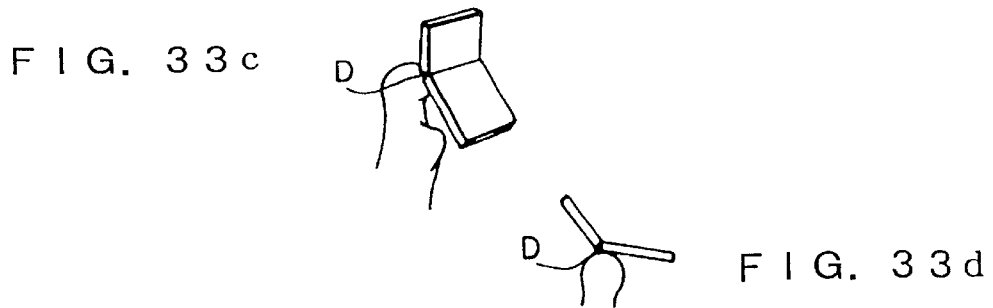
FIG. 33c
FIG. 33d

FULL REPRODUCTION ARTICULATOR

This application is a continuation of now abandoned International Patent Application No. PCT/JP98/04764, filed Oct. 21, 1998, designating the U.S., which was published under PCT Article 21(2) in Japanese, and claims the benefit of the filing date of Japanese Patent Application No. 12-131931 filed on May 14, 1998.

BACKGROUND OF THE INVENTION

1. Field of the Invention

The present invention relates to an articulator that is used to reproduce human jaw movement, in particular articulation, when dental prostheses (for example, dentures etc. to replace lost teeth) are constructed.

2. Description of the Related Art

Previously known articulators will be described below, together with their limitations.

(1) What an Articulator is

The jaw performs the functions of eating and speaking etc. and, in order to achieve these functions, performs truly many different types of movement. Construction of dental prostheses is an important technique in dental treatment in order to recover lost function, and in this connection, it is important to have a good understanding and grasp of jaw movement. Thus, reproduction of jaw movement is indispensable in order to achieve good insertion of the dentures, good articulation of the upper and lower rows of dentures, and good chewing movement.

There is a considerable degree of individuality as regards the chewing movement of individuals. In order to construct good dentures, a device for reproducing jaw movement, in particular articulation, i.e. an articulator is indispensable, and a great amount of efforts is being made to develop these devices. However, an accurate full reproduction articulator corresponding faithfully to the jaw movement of individual persons has not yet appeared.

(2) Conditions for Articulation Reproduction

In reproducing (characterizing) the movement of any object, not only the jaw, the start and end positions of movement of the object should be characterized. Specifically, if the position prior to movement of an object K is K0 and its position after the movement is K1, the change of position K0→K1 constitutes the movement of the object K. If the jaw is thought of as a rigid body, the position of the rigid body as a whole i.e. the jaw is characterized by characterizing the positions of three points of the rigid body. Clinically, the three points A, B, C shown in FIG. 26 of the accompanying drawings are employed for these three points, but this is for the sake of convenience, and any points on the rigid body including the jaw could be used. Referring to FIG. 27, if the positions prior to and after the movement are respectively indicated as A0, B0, C0 and A1, B1, C1, the jaw movement can be reproduced by characterizing A0, A1, B0, B1 and C0, C1 (see the arrows in FIG. 27).

(3) Terms Used to Describe Occlusion

Referring to FIG. 28, in dentistry, general terms such as front plane, side plane and horizontal plane are replaced by frontal plane, sagittal plane and occlusal plane, respectively. Also, the area where movement of the jaw occurs is termed the working side, and the opposite area is termed the non-working side (or balancing side). Although in recent years the term "balancing side" has tended to become obsolete, in this characterization, this side will be referred to as the "balancing side".

The jaw consists of the maxilla and mandible and chewing is performed by articulation of the respective teeth. The maxilla is included in the skull, while the mandible is suspended by muscles and tendons from the cranium, so that only the mandible is moved. The mandible consists of the row of teeth, the body of mandible, and the condyles. In FIG. 28, the condyle at point A is the condyle on the movement side, and so is called the working side condyle, while the condyle at point B is called the balancing side condyle. In the middle of the mandible, i.e., the incisal region, the mesial point of central incisors on the left and right is called the incisal point, and the center point of the condyle is called the condylar point. Reproduction of chewing movement is characterized by the three points: left and right condylar points and the incisal point.

(4) Mandibular Movement a) Incisal Path and Condylar Path

Mandibular movement is performed in five directions, namely, protrusively, laterally to left and right, opening and posteriorly. In this process, as shown in FIG. 29, movement of the condyle is regulated by the form of the associated joint cavity in which the condyle is accommodated. The line joining the left and right condylar points is called the "intercondylar axis". When the two condyles perform sliding movement over the surfaces of the joint cavities, the incisal points can perform rotary movement about the occasional intercondylar axis. The loci of the movement of the condylar points and the incisal point are respectively called the condylar path and incisal path.

b) Protrusive Movement

When protrusive movement is performed, as shown in FIGS. 29 and 30, the condyles move anteriorly and downwards along the shape of the joint cavities. This is on average about 30 degrees (30°) with reference to the occlusal plane, and is called the inclination of sagittal condylar path during protrusive movement, abbreviated to the inclination of protrusive sagittal condylar path. The protrusive sagittal condylar path inclinations are often different between the left and right condyles. The incisal point likewise moves anteriorly and downwards, constrained by the shape of the incisors of the maxilla. The clinical reference value with respect to the occlusal plane is 10°.

c) Lateral Movement

As shown in FIG. 31, in the case of lateral movement (where the jaw moves to left or right), the balancing side condyle executes a large movement for what is only a slight movement of the working side condyle. Like the protrusive movement, the balancing side condyle executes anterior and downwards movement along the shape of the joint cavity; the inclination of sagittal condylar path when this movement happens is called the lateral sagittal condylar path inclination and is generally larger than the protrusive condylar path inclination, the difference of these angles being termed the Fischer angle (considered to be about 15° on average).

Also, during lateral movement, the working side condyle is known to move outwards in the working direction. This outward movement is called "Bennett movement" after the name of its discoverer. Since the mandible is unitary, if the working side condyle moves outwards, the balancing side condyle is pulled inwards. As a result, the balancing side condyle moves forward, downwards and inwards. The inwards angle with respect to the sagittal direction i.e. the angle of lateral condylar path is called the "Bennett angle".

(5) Characterization of Mandibular Movement

If it can be characterized to what extent the three points (left and right condyles and incisor) move vertically, left/ right and anteriorly/posteriorly, the entire mandibular movement can be characterized. Also, the direction of movement of a given point is the direction of the line of intersection of the two planes that characterize the direction of movement of that point. That is, two planes are necessary and sufficient in order to characterize the direction of movement of a given point.

Hereinbelow, the planes that characterize the three points (left and right condyles and incisor) will be described.

As already stated, the mandibular movement is effected in opening, protrusively, posteriorly, and laterally (working side and balancing side). Of these, mouth-opening movement is a movement to release occlusion, so this may be excluded from the requirements for the articulator. Also, if the characterizing plane for protrusive movement is used for posterior movement, it would be sufficient to obtain planes characterizing the three movements: protrusively, working side and balancing side. Since two planes are required for a single movement in respect of each point, reproduction of the three types of movement by each point requires six planes. Also, if the positions of the two condylar points are characterized, the left and right and anterior/posterior positions of the incisal points are relatively characterized from the two condylar points and the amount of vertical opening thereof is characterized by arbitrary choice of the technician/doctor or contact of the upper and lower plaster models, so the subject of consideration in regard to reproduction of jaw movement need be only left/right lateral movement of the condyles. Furthermore, in the case of protrusive movement, what is necessary is a single plane to characterize sagittal condylar path inclination, so in fact only five planes are required. Also, since the position of the incisal point is relatively characterized from the two condylar points after the positions of the two condylar points are characterized, and, furthermore, the setting of the amount of mouth opening at the incisal point is arbitrary, the subject of consideration in regard to reproduction of jaw movement need only be the movement of the left and right condyles. In sum, for reproduction of jaw movement in an articulator, what is necessary is only reproduction of the three movements: protrusive, balancing side and working side of the condyles. As mentioned above, for protrusive characterization, a single plane is sufficient, and it is satisfactory if movement of each of the left and right condyles can be characterized by five characterization planes, respectively.

Also, the three-dimensional movement characterization elements of the condyles are as follows:

Vertical characterization: sagittal condylar path inclination plane

Internal/external characterization: Bennett plane

Anterior/posterior characterization: rear wall (6) Mechanism of Conventional Articulator and Problems Thereof FIG. 32 shows the condition when the jaw is moved to the right. The balancing side condyle moves in the anterior, downwards and inwards direction, the amount of its movement being characterized by two angles (planes), namely, the balancing side sagittal condylar path inclination and the angle of balancing side lateral condylar path (Bennett angle).

That is, the vertical characterization of the balancing side condyle is achieved by the balancing side sagittal condylar path inclination, and inner/outer characterization is characterized by means of the Bennett angle.

In contrast, while the working side condyle is pushed outwards due to the Bennett movement (inside/outside characterization is characterized by the Bennett angle of the balancing side condyle), the remaining anterior/posterior characterization and vertical characterization are characterized in the conventional articulator by a rear wall and working side sagittal condylar path inclination plate by adjustment using a screw M in FIG. 7 or a screw in FIG. 32 (the one corresponding to the screw N in FIG. 7). That is, as shown in FIG. 32 or 7, lateral movement is characterized by four plates (four angles).

However, because the movement is not only to be to the right but to left and right, a "full reproduction articulator" is not so easy to achieve. This is because although up to this point only the case where the jaw was moved to the right was considered, the same adjustment as was considered above must now be performed also when the jaw is moved to the left. The working side sagittal condylar path inclination that was employed for vertical characterization when the right condyle was the working side condyle cannot be employed as the balancing side sagittal condylar path inclination when the right condyle now becomes the balancing side condyle. In general, the working side sagittal condylar path inclination and the balancing side sagittal condylar path inclination are different, so it is not possible to represent the vertical characterization of the working side condyle and the sagittal condylar path inclination of the balancing side condyle by a single sagittal condylar path inclination plate. It is not possible to satisfy both the working side and balancing side by a single sagittal condylar path inclination plate. This is because a single plane cannot be used to characterize different movements at the same time.

Consequently, with a conventional articulator, it is necessary to adjust the dentures by adjusting the articulator for the case of mandibular movement to the right side, then to perform adjustment of the articulator once more for the case of mandibular movement to the left side. Since avoiding the problem of excessive time being required for the re-adjustment, conventionally, the sagittal condylar path inclination of the balancing side is also used for the sagittal condylar path inclination of the working side.

Methods of Characterizing the Working/balancing Sagittal Condylar Path Inclination Using a Single Sagittal Condylar Path Inclination Plate (i) Method of Dividing a Plate of the Sagittal Condylar Path Inclination In order to overcome this difficulty, a sagittal condylar path inclination plate divided as shown in FIGS. 33a and 33b to provide separate sagittal condylar path inclination plates during working and during balancing respectively might be proposed. However, with this method, if the inclination during working is greater than the inclination during balancing, as shown in FIGS. 33c and 33d, a groove D will be produced which makes smooth movement of the condyle impossible to reproduce. Namely, a sagittal condylar path inclination plate can be used to characterize only one between vertical characterization of the working side condyle or characterization of the amount of descent of the balancing side condyle. Detailed reasons will be given later, but here it will be simply stated that it is the wisest course from the point of view of convenience to employ a sagittal condylar path inclination plate to characterize the amount of descent of the balancing side condyle.

(ii) Method of Rotating the Sagittal Condylar Path Inclination Plate About the Condylar Path Inclination Axis The following passages deal with a method adopted in an articulator which is currently known as a full-adjustable articulator. As shown in FIG. 7, both the angle of the balancing side sagittal condylar path inclination and the angle of the working side sagittal condylar path inclination can be characterized by a single condylar path inclination plate, according to use of both adjustments of a condylar path inclination plate in two ways, sagittal balancing side condylar path inclination is characterized by rotating the plate about the intercondylar axis as a center axis (N in FIG. 7), and sagittal working side condylar path inclination is characterized by rotating the plate (hereinbelow called the Fischer sliding) about the axis, which is defined by the intersect of the condylar path inclination and sagittal plane, as a central axis (M in FIG. 7).

However, this current method has the following problems.

(7) Points which Require Improvement in the Conventional Articulator (a) Reproduction of the Fischer Angle In order to fully reproduce jaw movement, the protrusive movement must also be reproduced. There is a problem in this respect. When the jaw moves protrusively, the left and right condyles move anteriorly and downwards with the inclination of the protrusive sagittal condylar path. As described above, the inclination of the protrusive sagittal condylar path during protrusive movement and the inclination of the sagittal condylar path during lateral movement are different, in general. Consequently, the condylar path inclination plate would have to represent three condylar path inclinations, namely (1) the balancing side condylar path inclination, (2) the working side condylar path inclination and (3) the protrusive condylar path inclination; however, this is impossible. By using the Fischer slide, it is possible to represent the following two inclinations: (1) balancing side condylar path inclination and (2) working side condylar path inclination. But this approach can also be used to represent (1) balancing side condylar path inclination and (3) protrusive condylar path inclination. Two inclinations may be adopted among these three, and the best course is to represent (1) balancing side condylar path inclination and (3) protrusive condylar path inclination. The reason for this is that if (2) the working side condylar path inclination is adjusted after setting (1) the balancing side condylar path inclination, the previously adjusted (1) balancing side condylar path inclination changes. Mutual adjustment interferes with mutual setting. On the other hand, if the protrusive condylar path inclination is set in the first place, and then, the working side condylar path inclination is set by using the screw M (FIG. 7), there is no change of the protrusive condylar path inclination previously set. If this is done, it is necessary that the vertical characterization of the remaining working side condyle should be characterized by a mechanism which is independent from the condylar path inclination plate.

(b) Need of Reproduction of Posterior Movement

On a conventional articulator, posterior movement cannot be performed. In this background, there has been a conventional theory of the "centric relation concept" in which the rear most position of the mandible is the best and beyond which further retrusion was not possible as the starting point. However, in fact, the actual mandible does perform a slight retruded movement. There are many patients of the temporomandibular arthrosis whose cases are thought to be caused by dental prostheses making injurious occlusal contact in retruded movement. On the conventional articulator, retruded checking is impossible. Even dentists could not tell whether there would be early contact on retruded movement, without inserting the dental prosthesis in the oral cavity. It is considered be significant to be able to perform retruded movement on the articulator at the stage of construction of the dental prosthesis and to be able to check whether there is injurious occlusal contact during retruded movement.

(8) Summary

Conventionally, there are various types of full-adjustable articulators, and these have various respective characteristics in detail, but their basic principles are common, enabling the following five elements to be characterized:

(i) Distance Between the Condyles (first element)
(ii) Balancing Side Condyle
(1) Sagittal Condylar Path Inclination Plate (second element)
Vertical characterization
(2) Bennett Plate (third element)
Internal/external characterization
(ii) Characterization of Working Side Condyle
(3) Rear Wall (fourth element)
Anterior/posterior characterization
(4) Fischer Slide (fifth element) (rotation of sagittal condylar path inclination plate about sagittal condylar path axis)
vertical characterization The above conventional characterizations do not include condyle characterization during protrusive movement. After the condylar path inclination plate has characterized two items, i.e., balancing side condylar path inclination and working side condylar path inclination, the third item of protrusive condylar path inclination cannot be characterized. The characterization of the distance between the condyles, which is the first of the above five elements, has no relationship with the characterization of condyle movement. The above five elements are therefore essentially only four. The characterization of the intercondylar distance is only useful in characterizing the center point of rotation of the lateral movement.

That is to say, full reproduction of condyle movement cannot be achieved with the above four characterizations. By this omission of the remaining one of the characterizations, protrusive movement cannot be reproduced because the characterization of the protrusive condylar path inclination is lost. In actual practice, the protrusive characterization is adjusted by partial grinding or adding thickness of the plate of sagittal condylar path inclination. The reason for the necessity for grinding or adding is that the Fischer slide is used for vertical characterization of the working side condyle.

As described above, even conventional articulators known as full-adjustable articulators, cannot, in fact, reproduce protrusive movement of the jaw. Since today's dental prostheses constructed on the conventional semi-adjustable articulators do not harmonize with the actual chewing movement of mandible at all, they often give an uncomfortable sensation. From the view of the above clinical circumstances, an object of the present invention is to provide a full reproduction articulator which is capable of reproducing faithfully and accurately the entire jaw movement, in particular the articulation, including individual differences.

As another object of present invention, this articulator should be provided not only for faithful and accurate reproduction of jaw movement, but also for clinical means of treatment. In cases where faithful and accurate reproduction would cause injury to the body, the articulator must be capable of providing new ideal mandibular positions and new ideal pattern of jaw movement.

Namely, by means of a remount function, the mandibular plaster model can be transferred to an ideal optimum position on the articulator from a position mounted faithfully and accurately just as in the current condition of the mandible, and if necessary, can be returned at any time to the previous actual position from the optimum position.

SUMMARY OF THE INVENTION

According to one aspect of the present invention, there is provided a full reproduction articulator comprising: a mandibular model member, a base erected on the mandibular model member, two condyle balls projecting from the base, a maxillary model member that occludes the mandibular model member, and condyle boxes linked to both sides of the maxillary model member for regulating movement in the anterior/posterior direction, movement in the left/right direction and movement in the vertical direction of the maxillary model member by contacting the two condyle balls; wherein independently of the working side condyle box, there is further provided on the base a Bennett lift mechanism that lifts the maxillary model member from the working side condyle ball when the maxillary model member moves laterally in the left/right direction.

Preferably each of the condyle boxes includes a sagittal condylar path inclination adjustment plate, Bennett plate and rear wall plate, each plate being freely adjustable in angle. The sagittal condylar path inclination adjustment plates preferably regulate vertical movement during anterior/posterior movement by contacting the heads of the two condyle balls. The Bennett plate preferably regulates left/right movement by contacting the inside face of the balancing side condyle ball. The rear wall plate preferably regulates anterior/posterior movement by contacting the posterior part of the working side condyle ball. Furthermore, preferably the condyle boxes are respectively removably provided on the maxillary model member.

Preferably the lift mechanism includes cam members each having an adjustable angle cam face mounted on one of said base or maxillary model member and pins formed on the other of said base or maxillary model member and contacting the cam faces of said cam members.

Preferably the lift mechanism includes fixing means that fix the cam members to the base or maxillary model member after angular adjustment of the cam faces. Preferably the pins are arranged on the base or maxillary model member in such a way that their projecting length is adjustable.

According to another aspect of the present invention, there is provided a full reproduction articulator comprising: a mandibular model member, a base erected on the mandibular model member, two condyle balls projecting from the base, a maxillary model member that occludes the mandibular model member, and condyle boxes linked to both sides of the maxillary model member for regulating movement in the anterior/posterior direction, movement in the left/right direction and movement in the vertical direction of the maxillary model member by contacting the two condyle balls; wherein the mandibular model member includes a mandibular position remounting mechanism that makes it possible to remount the position of a lower denture model with respect to the maxillary model member.

Preferably the mandibular model member includes a mandible plate and a lower denture model provided on this plate. Preferably the lower denture model is provided with a mounting plate, and this mounting plate is mounted on the plate so as to be capable of being remounted in position on the plate by means of a mandible remounting mechanism. The mandible remounting mechanism preferably includes a plurality of adapters that engage the mounting plate and fixing means that locate and fix the adapters in position on the mandible plate together with the mounting plate.

Preferably the two condyle balls are provided on a base in such a manner that their height is adjustable. The maxillary model member preferably has an incisal pin of freely adjustable height that sets the incisal point of the upper and lower denture models by contact with the mandible plate of the mandibular model member.

Preferably means are provided to variably adjust the distance between the left and right condyle boxes when, in order to correct the jaw position, the lower denture model can be moved on the mandible plate surface, and the height of the incisal pin can be adjusted, and the height of the condyle ball can be adjusted, too.

BRIEF DESCRIPTION OF THE DRAWINGS

FIG. 3a illustrates a cross-sectional view taken along A—A in FIG. 2;

FIG. 3b illustrates a perspective view of a screw;

FIG. 6 is a perspective view showing the movement of a condyle ball in a condyle box;

FIG. 7 is a schematic diagram useful to explain adjustment of jaw movement in a condyle box;

FIG. 8 is an exploded perspective view showing another embodiment of a condyle box according to the present invention;

FIG. 9 is a perspective view of modification derived from the embodiment shown in FIG. 8;

FIG. 10 is a perspective view likewise showing another modification;

FIG. 11 is a perspective view showing a component of the part shown in FIG. 10;

FIG. 12 is a perspective view seen from the direction C in FIG. 11;

FIG. 17 is a view seen from the direction E in FIG. 16;

FIG. 18 is a view showing a detail of yet another embodiment of the present invention;

FIG. 21 is an overall perspective view showing yet another embodiment of the present invention;

FIG. 22 is a diagram given in explanation of superimposition of upper and lower denture models in FIG. 21;

FIG. 32 schematically illustrates a construction of a conventional articulator; and FIG. 33a to FIG. 33d respectively are views given in explanation of problems that arise due to the sagittal condylar path inclination plate being given two angles of inclination on balancing and on working.

DETAILED DESCRIPTION OF THE INVENTION

The chief characteristics of a full reproduction articulator according to an embodiment of the present invention are firstly that vertical characterization of the working side condyle is adjusted independently from the sagittal condylar path inclination plate and, secondly, that it is arranged to permit reproduction of the Fischer angle. A major feature is that this articulator can cope with cases where the mandibular position must be revised during use of the articulator. The reason of this necessity is that there are many case where, from the beginning, the positional relationship between the temporomandibular joint and the mandible is not correct and distorted clinically.

A full reproduction articulator according to an embodiment of the present invention is described below with reference to the appended drawings.

I. Construction of the Articulator
1) Outline

Figure 1:
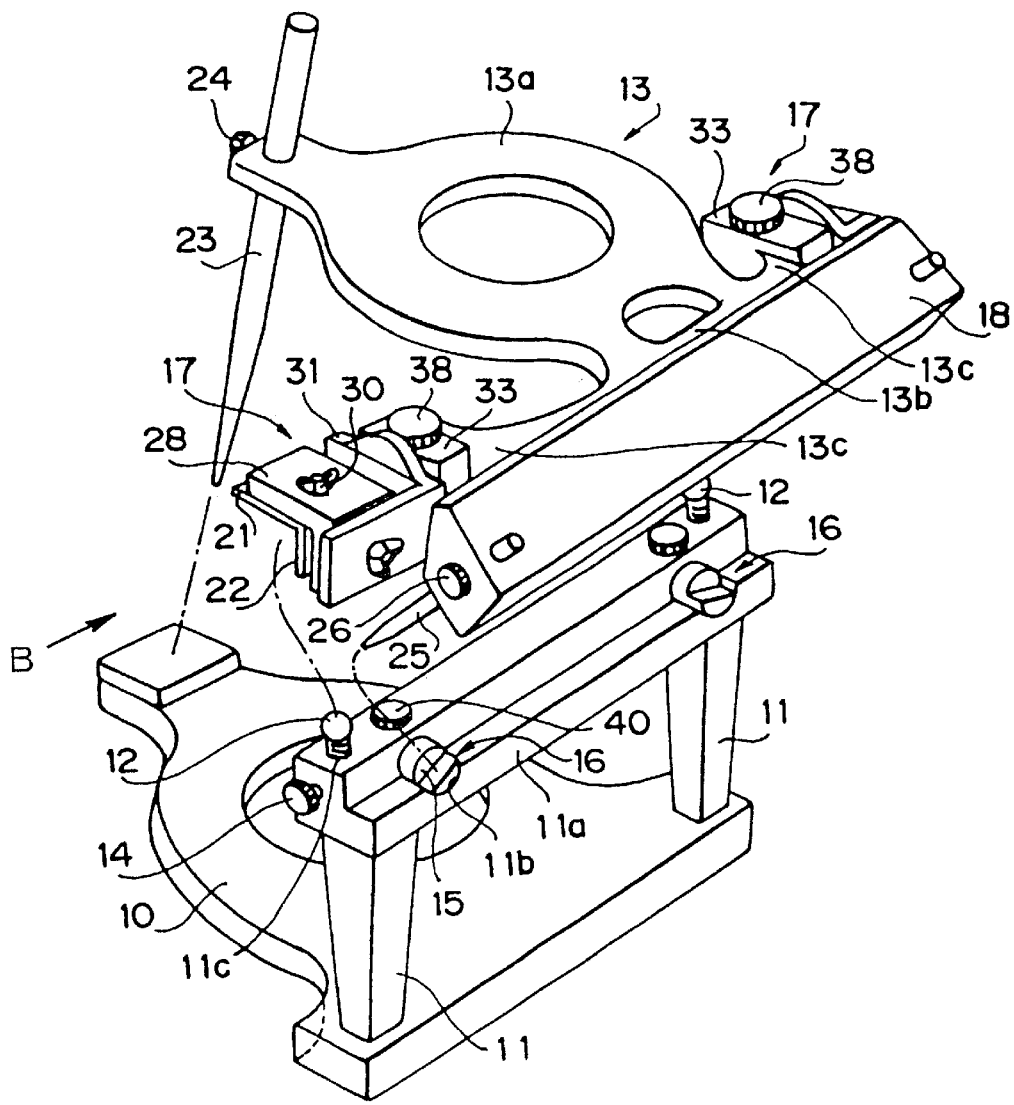
FIG. 1 illustrates an embodiment of a full reproduction articulator according to the present invention.

As shown in FIG. 1, the articulator essentially includes: a plate-shaped mandibular model member 10 on which a lower denture model (not shown) is set; a gate-shaped base 11 which is erected on this mandibular model member 10; two condyle balls 12 projecting from the lintel 11a of this base 11; and a plate-shaped maxillary model member 13 which receives the upper denture model (not shown) and is linked to these condyle balls 12 through a condyle box 17. The condyle box 17 regulates movement in the anterior/posterior direction, left/right direction, and vertical direction.

The condyle balls 12 are the condyles of the mandible, but they need not necessarily have the same intercondylar distance as in the body. The base part of each condyle ball 12 is rod-shaped and a scale is cut in the rod-shaped part. They are inserted in holes formed in the base 11, the height of the condyle balls 12 being adjustable by adjusting the amount of this insertion and fixing by means of screws 14.

Maxillary model member 13 includes a main body 13a, projecting parts 13c integrally formed at the sides of base 13b of this main body 13a, and a block member 18 that is approximately trapezium-shaped and is fixed to base 13b.

At the tip of main body 13a, there is mounted an incisal pin 23 that regulates movement of maxillary model member 13 in the downwards direction, the length of its projection being adjustable by screwing or unscrewing screw 24.
2) Condyle Box Condyle boxes 17 are releasably mounted on the two projecting parts 13c of maxillary model member 13. These condyle boxes 17 contact the left and right condyle balls 12, 12 respectively so as to regulate anterior/posterior, left/right and vertical movement of maxillary model member 13 during the jaw movement.

Figure 2:
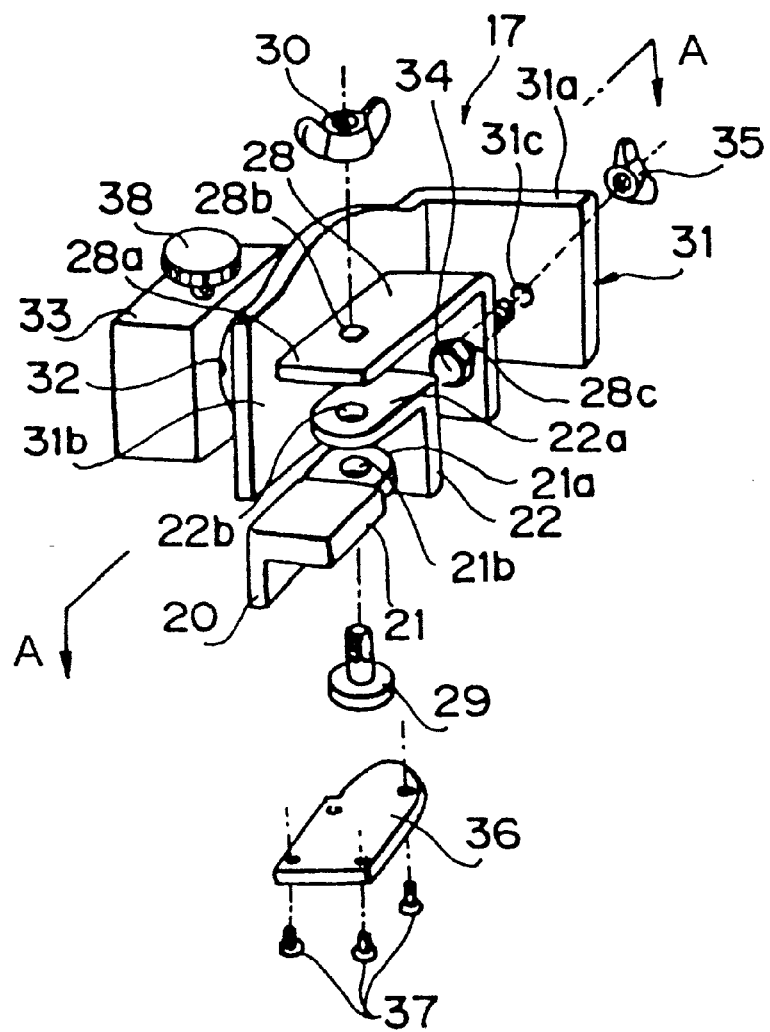
FIG. 2 illustrates an exploded perspective view of major portions shown in FIG. 1.

As shown in FIG. 2, the condyle box 17 includes a Bennett angle adjustment plate 20 that makes possible adjustment of the Bennett angle by contacting the balancing side condyle ball 12; a sagittal condylar path inclination adjustment plate 21 that makes possible adjustment of the sagittal condylar path inclination, being integrally formed with this Bennett angle adjustment plate 20; and a rear wall member 22 that makes possible adjustment of the working side condyle ball 12 in the anterior/posterior movement direction.

A bearing block 33 is integrally provided on each projecting part 13c of the maxillary model member 13, a shaft 32 provided on the inside face 31b of each L-shaped condyle member 31 is inserted in the associated bearing block 33, and each condyle member 31 is releasably mounted on the bearing block 33 such that its angle of rotation is adjustable by screwing/unscrewing a screw 38 that is screwed into the bearing block 33.

On the posterior face 31a of this condyle member 31, an L-shaped support member 28 is provided in a manner free for adjustment of rotational position. Specifically, a through hole 31c is formed in the side 31a of the condyle member 31, and a butterfly nut 35 is screwed on to the screw 34 after inserting the screw 34 from the anterior side of the support member 28 in the through-hole 28c and through-hole 31c. In this way, the support member 28 is supported such that it is rotatable about the axis of the screw 34.

Mounted on this support member 28, mounted are the rear wall member 22 and sagittal condylar path inclination adjustment plate 21 that are integrally formed with the Bennett angle adjustment plate 20, their angle being freely adjustable by means of screw 29 and butterfly nut 30.

Specifically, as shown in FIG. 3a, on the sagittal condylar path inclination adjustment plate 21, there is formed an extension 21a parallel to the plate face; on the rear wall member 22, there is formed an extension 22a perpendicular its plate face; and in the extensions 21a, 22a, there are formed mutually corresponding through-holes 21b, 22b. On the other hand, in an upper side 28a of the support member 28, there is formed a practically semicircular through-hole 28b corresponding to the through-holes 21b, 22b; these are integrated by screwing the butterfly nut 30 on to the screw 29 after inserting the screw 29 from the mandible in the figure into the through-holes 21b, 22b, 28b.

As shown in FIG. 3(b), the screw 29 has a head 29a and a shaft 29b connected thereto. A threaded part 29c is formed only in the vicinity of the tip of the shaft. The threaded part 29c is partly cut to form a cut portion 29d. By fitting this cut portion 29d into the through-hole 28b of the support member 28, rotation of the screw 29 itself is prevented, so as to permit only rotation of the sagittal condylar path inclination adjustment plate 21 and rear wall member 22 with respect to the support member 28.

Also, on the undersurface of the sagittal condylar path inclination adjustment plate 21, a screening plate 36 is fixed by means of screws 37. The head 29a of the screw 29 is thereby covered and hidden by the screening plate, and the condyle ball 12 and screw 29 are prevented from contacting.

In this condyle box 17, the sagittal condylar path inclination of the sagittal condylar path inclination adjustment plate 21 can be adjusted by unscrewing the screw 38 and adjusting the angle of rotation of the condyle member 31, and the Fischer slide can be adjusted by adjusting the angle of rotation of the support member 28 by means of the screw 34 and butterfly nut 35. Further, the Bennett angle can be adjusted by rotating the Bennett angle adjustment plate 20 about the screw 29 and the rear wall angle can be adjusted by rotating the rear wall member 22 about the screw 29.

The appearance of the Fischer angle using this mechanism will now be described with reference to FIG. 6.

FIG. 6 shows the movement of the condyle in the temporomandibular joint cavity; in terms of the articulator, it shows the movement of the condyle balls in the condyle box; this figure shows the left temporomandibular joint or condyle box from the front upper left inclined direction.

It should be assumed here that a sagittal condylar path inclination plate J is inclined (rotated) with respect to the front head face. In relative terms, when the condyle moves forward from F to G along the gradient of the sagittal condylar path inclination plate J, movement takes place from F1 to G1 in the occlusal plane and from F2 to G2 in the sagittal plane.

Next, in the event of movement in the direction of the balancing side (movement in the rightwards direction in the drawing i.e., when facing, towards the left), the condyle on the balancing side moves from F to H. In this case, on the occlusal plane, movement takes place from F1 to H1 and the angle of the line (F1→G1) and the line (F1→H1) is the Bennett angle. In the sagittal plane, movement takes place from F2 to H2 and descends deeply along the inclination than the path (F2→G2) in the protrusive movement, with the result that the sagittal condylar path inclination becomes larger. That is, it is known that the line (F2→H2) of lateral movement is different from the line (F2→G2) of protrusive movement, and the difference between these lines (F2→G2) and (F2→G2) is called the Fischer angle; clinically, as mentioned above, its mean value is taken to be 15°.

3) Bennett Lift

In addition to this function of the condyle box 17, according to the present invention, there is provided a Bennett lift mechanism 15 that enables to specify the vertical position of the working side condyle 12, and this mechanism is independent of the restriction of the sagittal condylar path inclination adjusting plate 21 of the working side condyle box 17 in the event of lateral movement i.e. when the condyle ball 12 on the balancing side is sliding whilst in contact over the sagittal condylar path inclination adjusting plate 21 of the balancing side condyle box 17. In this case, the working side condyle is separated from the regulation of the sagittal condylar path inclination plate of the condyle box 17, with the result that the working side maxillary model member 13 rises upwards from the working side condyle. This will be called "Bennett lift" and its mechanism will be called the "Bennett lift mechanism".

The clinical significance of this will now be described.

As shown in FIG. 7, when the balancing side condyle moves along the gradient of the sagittal condylar path inclination plate J and Bennett plate K, the condyle on the working side, although there are individual differences in the anterior/posterior direction, moves, in general, downwards rather than upwards, in the vertical direction, in the case of natural occlusion.

This downwards movement of the working side condyle is a phenomenon that was discovered by Bennett and which will be called the Bennett lifting movement. Bennett's experiments indicate "when lateral movement takes place whilst the upper and lower teeth are in articulation, the condyles move away from the joint cavities more than in the case where lateral movement takes place with the teeth not in articulation."

This means that, when, masticatory force is applied during lateral movement, if teeth are present, the condyles do not directly strike the joint cavity i.e. the presence of teeth are directly linked to protection of the temporomandibular joint.

The Bennett lifting mechanism 15 will be described with reference to FIGS. 1, 4 and 5.

This Bennett lifting mechanism 15 includes cams 16 belonging to the mandibular model portion provided on the base 11 behind the condyle balls 12 respectively, and pins 25 that belong to the maxillary model portion provided at both ends of the block member 18 that is the posterior of the maxillary model member 13.

At the back face of the lintel 11a of the base 11, there are formed two arcuate grooves 11b and cylindrical recesses 11c linked therewith. The cylindrical cams 16 are provided in the recesses 11b, 11c such that they are able to rock about the axes of the cams respectively. The cams 16 can be fixed on the base 11 by screwing in screws 40 that are screwed into the lintel 11a respectively. As shown in FIG. 5, each of the cams 16 includes a main body 16a of cylindrical shape fitted into the associated groove 11c and a cam face 16b formed by cutting away at the tangential position so as to contact the tip of a pin 25 always even if the main body 16a rotates. The tip of the pin 25 is of spherical shape, and the center of this sphere coincides with the center of rotation of the main body 16a. By forming the cam face 16b in a position tangential with respect to the semicircle at the tip of this pin 25, even when the main body 16a rotates, the pin 25 that is in contact with this cam face 16b does not move vertically due to the tangential position of the cam face 16b, so adjustment of the amount of lift can be accurately reproduced. The boundary portion of the main body 16a and cam face 16b is made capable of projecting 0 mm to about 4 mm from the outer face of the base 11. This enables posterior movement of the maxillary model member 13 on the working side. The angle of the cam face 16b can be altered by rotating the cam 16 about its axis.

Figure 4:
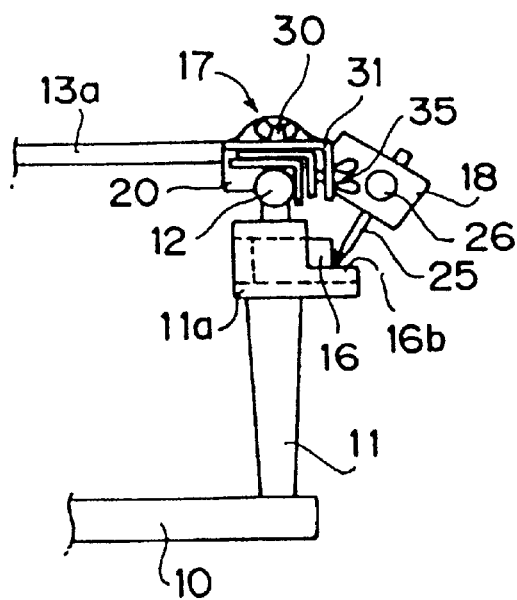
FIG. 4 is a view seen from the direction B in FIG. 1.

At both ends of the block member 18, the pins 25 are mounted so as to be capable of adjustment of their projecting length by screwing/unscrewing of screws 26; as shown in FIG. 4, they are arranged to contact the cam faces 16b of the cams 16 provided on the lintel 11a of the base 11. The pins 25 and cams 16 constitute the lifting mechanism of the present invention.

The function performed by such a mechanism will now be described.

In the event of lateral movement, the balancing side condyle ball 12 advances in the inwards, downwards and anterior direction whilst contacting the sagittal condylar path inclination plate of the maxilla part, so the cam 16 of the mandible part on the balancing side and the pin 25 of the maxilla part are separated. In contrast, the working side condyle ball 12 of the mandible part and the working side cam 16 are moved outwards with respect to the maxilla part, so, in relative terms, the condyle box 17 of the maxilla part and the working side pin 25 are moved inwards with respect to the mandible part. At this point, if the vertical characterized angle of the working side cam 16b is larger than the induced angle of the working side condylar path inclination plate, the working side pin 25 moves inwards while staying in contact with the cam face 16b. In this case, the working side condyle ball 12 descends relatively further below the maxilla part than would be caused by induction of the condyle path inclination plate. As a result, it is separated from and rises above the sagittal condylar path inclination adjustment plate 21 of the working side condyle box 17.

It should be noted that the extent of the separation/rising is to be determined by the actual condition of the joints and/or treatment policy. In rare cases, there may be instances where the working side condyle shows a deep descent into the joint cavity when the sagittal condylar path inclination is greater during working than during balancing. In such cases, it might be thought that the present articulator should be used with a shorter distance between the condyle balls, but reproduction of such deep descent into the joint cavity is dangerous for the body, so, clinically, induction is applied by a condylar path inclination plate during balancing so that such descent does not take place.

Namely, according to the present invention, in the reproduction of the protrusive movement and left/right lateral movement, adjustment of the sagittal condylar path inclination of the right and left condyle boxes, the right and left Bennett angles, and the right and left rear wall angles can be achieved respectively independently without mutual interference by introduction of the Bennett lift mechanisms and Fischer slide.

II. Operation of the Articulator

This is described below with reference to FIG. 1 through FIG. 6.

1) Initial Setting

First, a lower denture model is mounted by means of gypsum on a mounting plate (not shown), this mounting plate is mounted on the mandibular model member 10, and the mandibular denture model is fixed. Likewise, a mounting plate (not shown) on which the upper denture model is mounted using gypsum is mounted on the undersurface of the maxillary model member 13 and the maxilla denture model thereby fixed.

After this, as shown in FIG. 1, the condyle boxes 17 provided on both sides of the maxillary model member 13 are placed upon the condyle balls 12 provided on the base 11. In this process, as shown in FIG. 5, the tips of the two pins 25 projecting from the block member 18, which constitute the Bennett lift mechanism 15, are placed upon the cam faces 16*b* of the cams 16 provided on the base 11.

2) Method of Adjusting the Articulator

There are the following two main methods of adjusting the articulator.

i) Method of Adjustment
(1): Pantograph Method

In the body, there are individual differences as regards the shape, size and chewing movement of the jaw, so that unless the movement of the jaw is faithfully reproduced, perfect construction of dentures cannot be achieved. Accordingly, for the adjustment of the left and right condyle boxes 17, 17, namely, the adjustment of the angles of rotation of the condyle members 31 of sagittal condylar path inclination adjustment plates 21, support members 28, Bennett angle adjustment plates 20 and rear wall members 22, the movement of the lower jaw is measured beforehand by a graphical recording device. Using these measurement results, the left and right sagittal condylar path inclinations, Fischer slides, Bennett angles and rear wall angles are determined. Based on the resulting values, the left and right condyle boxes 17, 17 are adjusted, thereby achieving adjustment of the jaw movement matching individual differences.

ii) Method of Adjustment
(2): Check Bite Method

First, upper and lower tooth row models are mounted on the articulator in an occluded condition at the centric occlusion. Mounting is desirably effected by the split cast method. In the case of the check bite method, a face bow is unnecessary if the pantograph method is not introduced hereafter. The positional relationships of the upper and lower rows of teeth after movement are obtained using gypsum or resin etc. and the five planes are adjusted in the following sequence for reproduction on the articulator:

1. Left and right sagittal condylar path inclination plates during protrusive movement
2. Fischer slide of the balancing side condylar path inclination plate
3. Bennett plate
4. Working side rear wall
5. Cam face of the working side Bennett lift With the present articulator, there is no possibility of subsequent adjustments impairing earlier adjustments such as occurs in the conventional full-adjustable articulators.

3) Various Types of Movement and Adjustment of Condyle Boxes

Construction of dentures is performed by observation of the occlusion of the dentures as anterior/posterior, left/right, and vertical movement of the condyle boxes 17 of the maxillary model member 13 is effected relative to the condyle balls 12.

(a) Protrusive Movement

Protrusive movement of the maxillary model member 13 is performed in a condition with the left and right condyle balls 12 in contact and along the sagittal degree of inclination of the sagittal condylar path inclination adjustment plates 21 of the left and right condyle boxes 17,17.

(b) Lateral Movement

When performing lateral movement, on the balancing side, the condyle ball 12 moves in contact with the sagittal condylar path inclination adjustment plate 21 and Bennett angle adjustment plate 20 of the condyle box 17. On the working side, Bennett lift movement may be performed by the Bennett lift mechanism 15 on the working side independent of the sagittal condylar path inclination adjustment plate 21 of the condyle box 17. Specifically, the sagittal condylar path inclination adjustment plate 21 is raised from the condyle ball 12 as a result of movement of the pin 25 in contact with the cam face 16*b* of the cam 16. During this process, the rear wall member 22 of the condyle box 17 on the working side keeps contacting the condyle ball 12 and regulates the amount of protrusive or backward movement, even if the sagittal condylar path inclination adjustment plate 21 is separated from the condyle ball 12.

Also, although the pin 25 and cam 16 that constitute the Bennett lift mechanism 15 on the balancing side are in contact before commencement of the lateral movement, they become separated on lateral movement, so there is no possibility of their functioning.

4) Other Embodiments of Condyle Box (a) Crescent Type

Next, another embodiment of the present invention will be described. Structural elements that are similar to or identical with those of the previous embodiment are described by giving them the similar or same reference symbols.

FIG. 8 illustrates a modified example of the condyle box 17.

In the case of the condyle boxes 17 shown in FIGS. 1 and 2, the sagittal condylar path inclination adjustment plate 21 and Bennett angle adjustment plate 20, as well as the rear wall 22 are fixed to the support member 28 at a single location of the screw 29 and butterfly nut 30, but, in this modification, fixing can be effected at two locations.

First, the sagittal condylar path inclination adjustment plate 21 with the Bennett angle adjustment angle plate 20, and the rear wall 22 are supported in rotatable fashion on the supporting member 28 by means of screw 41 that is inserted into the through-holes 21*b*, 22*b*, 28*b*. Crescent-shaped through-holes 42, 43 are formed on either side of the screw 41 in the upper side 28*a* of support member 28. Corresponding to these through-holes 42, 43, the sagittal condylar path inclination adjustment plate 21 and an extension 22*c* of the rear wall member 22 have screw holes 21c, 22d formed therein. Screws 44, 45 are then inserted into the crescent-shaped through-holes 42, 43 respectively and threaded into the screw holes 21c, 21d respectively.

With this construction, when the heads of the screws 44, 45 are moved along the through-holes 42, 43 respectively, the sagittal condylar path inclination adjustment plate 21 with the Bennett angle adjustment plate 20 and the rear wall 22 are rotated about the screw 41 respectively. Fixing can be achieved by tightening the screws 44, 45, so that more secure fixing is insured. If a scale is provided along each of the through-holes 42, 43 as shown in the drawing, the Bennett angle and rear wall angle can be adjusted in a simple fashion by using the scale.

(b) Cylindrical Slide Type

In the case of the condyle box 17 shown in FIG. 9, the side face of the support member 28 is constituted as an arcuate face 28d, and the inside face of the condyle member 31 is constituted as an arcuate face 31d corresponding to the arcuate face 28d. The support member and condyle member are made slidable along these arcuate faces 28d, 31d. A through-hole 31e is formed in the condyle member 31, and fixing is effected by inserting a screw 50 into the through-hole 31e and screwing into a screw hole (not shown) formed in the arcuate face 28d of the support member 28.

With this modification, by sliding the support member 28 along the arcuate face 31d of the condyle member 31, the position of the support member 28 with respect to the condyle member 31 can be made to rotate about a virtual axis practically orthogonal to the shaft 32, thereby enabling the Fischer angle to be adjusted and enabling secure fixing to be achieved.

(c) Crab-claw Type

In the case of the condyle box 17 illustrated in FIG. 10 to FIG. 13, there is illustrated a modification of the support structure for the sagittal condylar path inclination adjustment plate 61, the Bennett angle adjustment plate 60 and the rear wall member 62.

Specifically, as shown in FIGS. 11 and 12, a groove 61a and extension 61b are formed on the sagittal condylar path inclination adjustment plate 61, and the Bennett angle adjustment plate 60 is integrally formed with the side face of the sagittal condylar path inclination adjustment plate 61. The rear wall member 62 is formed with a projection 62a that is freely slidably inserted in the groove 61a and with an extension 62b that extends outwards.

Figure 13:
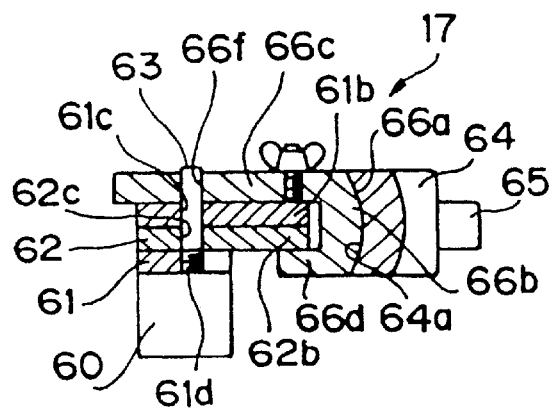
FIG. 13 is a cross sectional view taken along the line D—D in FIG. 10.

As illustrated in FIG. 13, in the upper part of the sagittal condylar path inclination adjustment plate 61 corresponding to the groove 61a, there is formed a through-hole 61c, and in the lower part there is formed a screw hole 6d at a position corresponding to the through-hole 61c. In the projection 62a of the rear wall member 62, there is formed a through-hole 62c corresponding to the through-hole 61c and screw hole 61d. The rear wall member 62 is made rotatable about a screw 63 with respect to the sagittal condylar path inclination adjustment plate 61 because the screw 63 is inserted into the through-holes 61c and 62c and screwed into the screw hole 61d.

Furthermore, a condyle member 64 is rotatably supported in the maxillary model member by means of shaft 65. An arcuate face 64a is formed on the condyle member 64 and a support member 66 is rotatably supported on this arcuate face 64a. Specifically, an arcuate face 66a corresponding to the arcuate face 64a is formed on a side plate 66b of the support member 66, so that rotation is possible by sliding the support member 66 on this arcuate face 64a. The support member 66 is arranged so as to be capable of being fixed to the condyle member 64 by means of a screw (not shown) and butterfly nut 67. A ceiling plate 66c is integrally formed with the side plate 66b of the support member 66, and an extension 66d is formed so as to project at a prescribed distance from this ceiling plate 66c. A screw hole 66e is formed passing through the ceiling plate 66c at a position corresponding to the extension 66d. The extension 61b of the sagittal condylar path inclination adjustment plate 61 and the extension 62b of the rear wall 62 are inserted between the extension 66d and ceiling plate 66c. The tip of the screw 68 projects from the screw hole 66e by screwing the screw 68 into a screw hole formed in the sealing plate 66c, so that the extension 61b of the sagittal condylar path inclination adjustment plate 61 and the extension 62b of the rear wall member 62 are gripped between the screw 68 and extension 66d. Accordingly, the sagittal condylar path inclination adjustment plate 61 and rear wall 62 are supported on the support member 66. Consequently, the sagittal condylar path inclination adjustment plate 61 and rear wall 62 are rotatable about the screw 63 and are integrally fixed to the support member 66 by being clamped between the extension 66d and screw 68. A through-hole 66f into which the screw 63 is inserted is formed in the ceiling plate 66c of the support member 66.

(d) Uniaxial Characterization System

Figure 14:
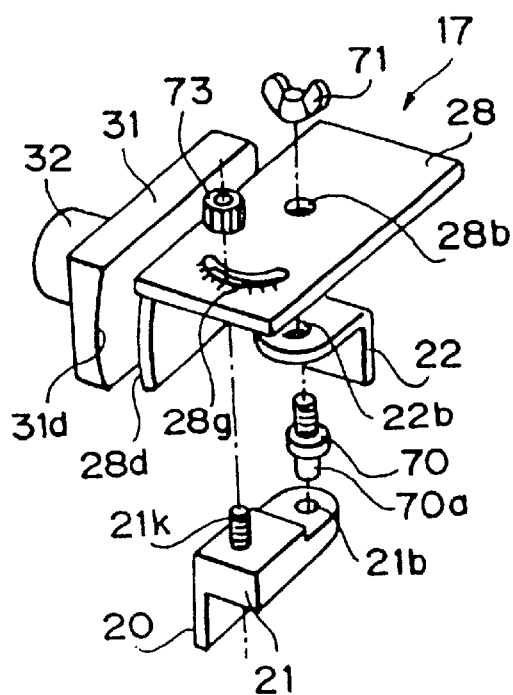
FIG. 14 is an exploded perspective view showing yet another embodiment of a condyle box according to the present invention.

The condyle box 17 depicted in FIG. 14 combines elements of the above embodiment and modifications. Specifically, the support member 31 is freely rotatably supported by the shaft 32 on the maxillary model member, and the support member 28 is supported on the condyle member 31 in such a manner that a curved face 28d formed on the support member 28 is in sidable contact with a curved face 31d formed on the condyle member 31. The rear wall member 22 is rotatably linked with the support member 28 by inserting a screw 70 from the side of the through-hole 22b into the through-hole 28b formed in the support member 28 and the through-hole 22b formed in the rear wall member 22, and by tightening a butterfly nut 71. A crescent-shaped through-hole 28g is formed in the support member 28, and a screw 21k projecting at the top face of the sagittal condylar path inclination adjustment plate 21 is inserted into the through-hole 28g while an unthreaded portion 70a formed at the tip of the screw 70 is inserted into the through-hole 21b formed in the sagittal condylar path inclination adjustment plate 21. The sagittal condylar path inclination adjustment plate 21 and Bennett angle adjustment plate 20 are mounted on the support member 28 by screwing a nut 73 over the screw 21k so that they are rotatable about the axis of the screw 70.

5) Further Bennett Lift Embodiment in Which the Location of Installation of the Bennett Lift Mechanism is Altered.

Figure 5:
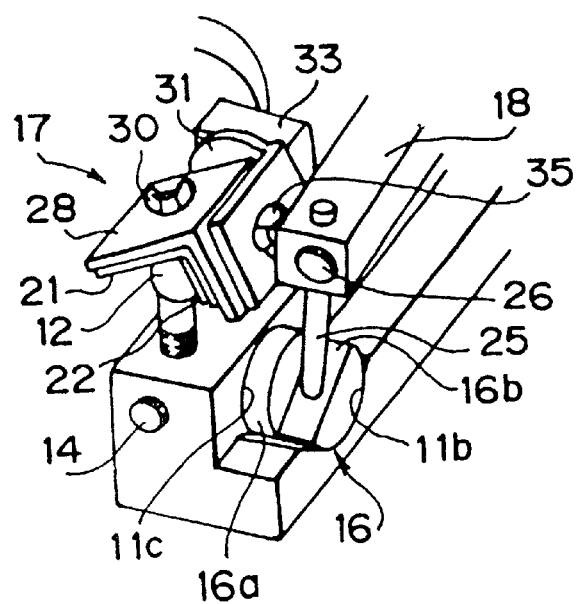
FIG. 5 is a perspective view showing a detail of FIG. 1.

Although, in the embodiment of FIG. 1, the Bennett lift mechanisms 15 are arranged between the condyle balls 12, the further inwards they are installed, the greater is the adjustment angle of the cams 16 that is required, so, as shown in FIG. 5, it is preferable to provide the mechanisms directly behind, or outside, the condyle balls 12 respectively.

(a) Arrangement with a Bennett Lift of 50 mm

Figure 15:
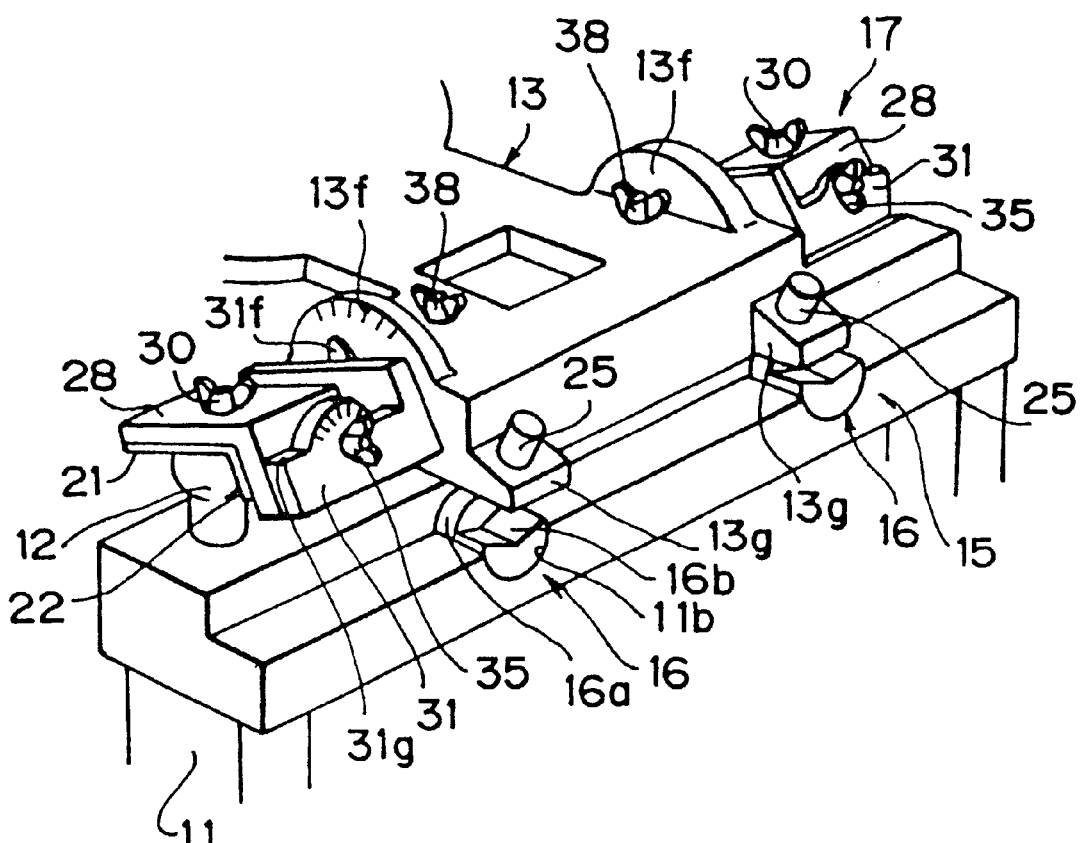
FIG. 15 is a perspective view showing yet another embodiment of the present invention.

FIG. 15 illustrates another embodiment of the present invention. This is, in general, equipped with a similar mechanism to the one shown in FIG. 1. The differences from that shown in FIG. 1 are as follows. It should be noted that each cam face is V-shaped and the associated pin 25 is half-withdrawn so as to expose the entire surface thereof.

A Cut-away portion 3g is formed at the rear end of each condyle member 31, so that the rear end of the support member 28 can be observed from the rear end side. A scale is provided on each cutaway portion 31g so that it is possible to know the relative rotation of the support member 28 with respect to the associated condyle member 31 from the relationship with a mark shown on the rear end of the support member 28. Also, a semicircular arcuate plate 13f is integrally mounted on the maxillary model member 13 adjacent each condyle member 31, and a projection 31f is formed at the side wall of each condyle member 31. Each plate 13f is provided with a scale so that it is possible to ascertain the relative rotation of the condyle member 31 with respect to the maxillary model member 13 from the relative relationship of the scale and projection 31f.

Figure 19:
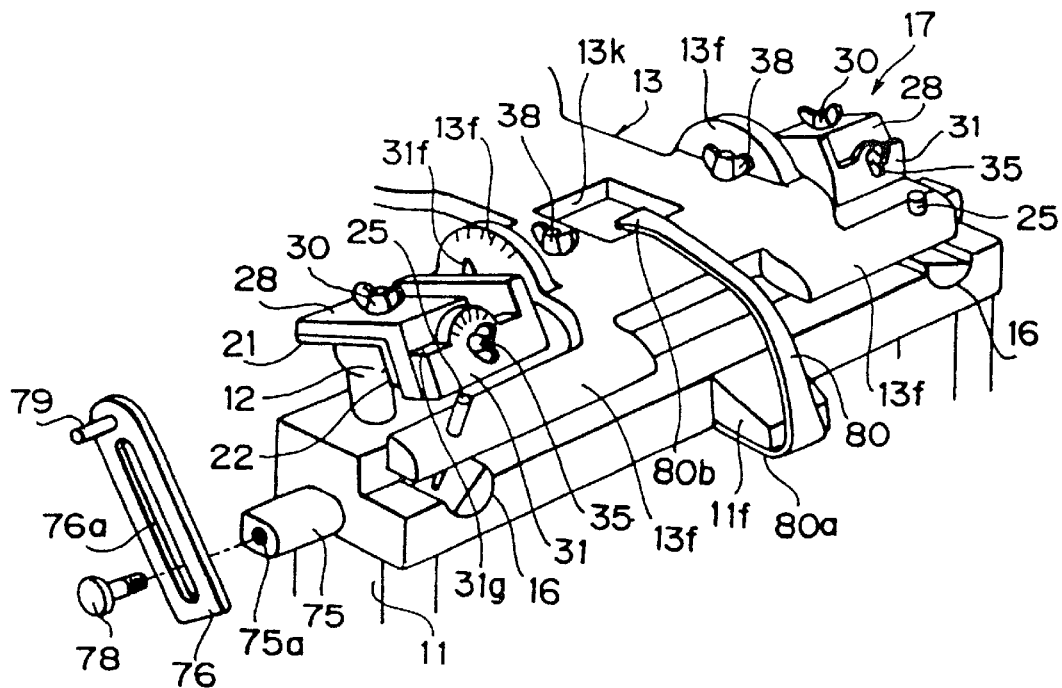
FIG. 19 is an exploded perspective view showing yet another embodiment of the present invention.

Also, two extensions 13g are formed at the rear end of the maxillary modeling member 13. The pin 25 is mounted in downwardly projecting condition on each of these extensions 13g. The distance between the bottom ends of the pins 25 provided on the extensions 13g is about 50 mm. This is about half the distance between the condyle balls 12. Stability is improved by employing a larger distance between the pins 25. However, if the pins are arranged so as not to interfere with the condyle members 31 etc., the dimensions of the posterior end of the maxillary model member 13 become large, tending to make the equipment inconvenient to handle. In this embodiment, therefore, they are arranged inside of the associated condyle members 31 etc. in order not to make the dimension of the posterior end of the maxillary model member 13 too large. It should be noted that making the distance between the pins 25 large is acceptable, and such embodiments are illustrated in FIGS. 16 and 19 (will be described).

(b) Arrangement with Bennett Lift of 70 mm

Figure 16:
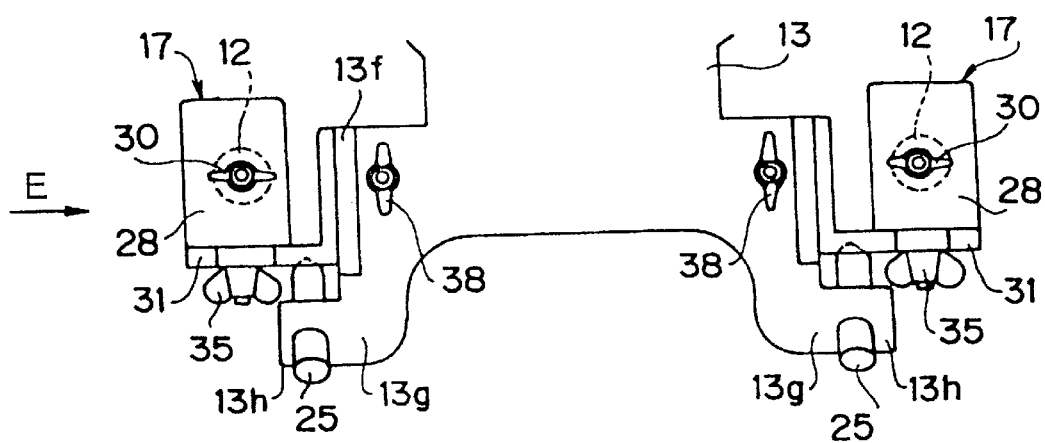
FIG. 16 is a plan view showing yet another embodiment of the present invention.

FIGS. 16 and 17 show yet another embodiment of the present invention. The difference as compared with FIG. 15 lies in that a further extension 13h extends outwards from each extension 13g formed at the posterior end of the maxilla model member 13, and the pin 25 is provided in the same way on each extension 13h. The distance between the pins 25 is about 70 mm. With this embodiment, stability and ease of operation of the maxillary model member can both be achieved.

(c) Arrangement with Bennett Lift of 110 mm

FIG. 19 shows an embodiment in which the pins 25 are provided outwards from the condyle balls 12. Stability is good, and the articulator is easy to move, but the increased length is troublesome in adjustment.

6) Arrangement of Pins 25

In the above embodiments, the pins 25 are arranged with an angle of about 45° with respect to the horizontal plane. If the maxillary model member 13 is opened by rotating through about 45°, the circumferential faces of the pins 25 contact the cam faces 16b making it impossible to open the maxillary model member 13 further. If, however, as illustrated in FIG. 18, the pins 25 are arranged in an erected condition close to perpendicular, the maxillary model member 13 can be opened practically to about 90°. The work of constructing the dentures is thereby made extremely easy.

7) V-shaped Cam

In the above embodiments, the cams 16 are employed having flat faces as part of the lift mechanism. If the movement of the pins 25 is to be regulated by such cams, the cam faces may have a V-shaped angle instead of flat as in FIG. 15.

8) The Same Object Could be Achieved by Interchanging the Pins of the Maxillary Moldel Member 13 with the Cams of the Mandible Member.

9) Other Auxiliary Structure (a) Mechanism for Linking a Graphical Recording Device FIG. 19 illustrates yet a further embodiment of the present invention. Graphical recording device linking members 76 that effect linkage to a graphical recording device are each mounted to a cap member 75, and there is also mounted to base 11 a biasing member 80 that pressure-biases the maxillary model member 13 such that the Bennett angle adjustment plates 20, sagittal condylar path inclination adjustment plates 21 and rear wall members 22 of the condyle boxes 17 provided on the maxillary model member 13 contact the condyle balls 12.

Specifically, extensions 13f that are longer than in FIG. 16 are formed at the posterior end of the right and left maxillary model members 13, and the tip of this extension 13f is releasably capped by the cap member 75. A screw 78 is threaded into a screw hole 75a formed at the other end of the cap member 75 to mount the graphical recording device linking member 76 in such a way that the linking member can perform rocking movement about the screw 78 and sliding movement along a slot 76a formed in the graphical recording device linking member 76. The graphical recording device linking member 76 is formed with a linking element 79 to which the graphical recording device is linked. The screw 78 is unscrewed, the linking element 79 of the graphical recording device linking member 76 is then positioned practically on the line passing through the centers of the condyle balls 12, and the screw 78 is tightened for fixing.

(b) Vertical Linkage Device

Figure 20:
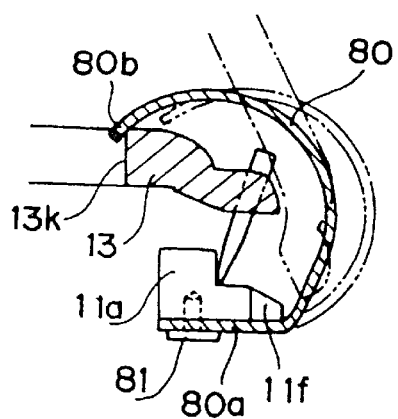
FIG. 20 is a cross-sectional view showing a detail of the structure shown in FIG. 19.

Also, as shown in FIGS. 19 and 20, a projection 11f is formed that extends posteriorly at the center of the posterior end of the lintel 11a. One end 80a of the biasing member 80 constituted by a plate spring bent into an arcuate shape is linked by a screw 81 to the undersurface of this projection 11f, and the other end 80b of the biasing member 80 is engaged with a ridge of a through-hole 13k formed in the maxillary model member 13. The maxillary model member 13 is biased downwards by the biasing member 80. Thus, when the maxillary model member 13 is opened in order to perform denture construction as shown by the double-dotted chain line in FIG. 20, the biasing member 80 flexes whilst remaining in contact with the ridge of the through-hole 13k. In this manner, opening and closure of the maxillary model member 13 are allowed.

In this embodiment, the graphical recording device (not shown) is linked to the linking element of the graphical recording device linking members 76 and the maxillary model member 13 is made to perform various movements in accordance with measurement results obtained by measuring beforehand the jaw movement. This is used to reflect the jaw movement of the body on the articulator. It would also be possible, as the construction for linking the graphical recording device, to form a wall on the outside face of the support member 28 and to arrange the linking element in projecting fashion on this wall.

III. Mechanism for Remounting the Mandibular Position

1) Functions Which an Articulator Must Possess as a Therapeutic Device

The full reproduction articulator of the present invention is not only simply a jaw movement reproduction device; it also serves as an analysis device to determine the status praesens and as a predictive device to predict the configuration that should be produced by treatment. Consequently, in consideration of its being a diagnostic/therapeutic device that can diagnose what treatment is necessary, it is desirable that clinical demands should be incorporated on an articulator as its mechanism.

Specifically, for temporomandibular arthrosis, it is necessary to be able to:

(1) extend the condyle balls in the vertical direction;
(2) perform movement in the posterior direction;
(3) remount the position of the mandible in any direction on the mandibular model member 10; and
(4) move and adjust the condyle boxes 17 in the outwards direction in order to correct a very small amount of inequality that is produced between the distance between the condyle balls and the distance between the condyle boxes. The position of the mandible is remounted three-dimensionally by satisfying the above (1) and (3) ability, but the distance inequality appears in this process. Preferably, these four adjustments are enabled for temporomandibular arthrosis.

Ability (1), (2) and (3) will now be described in connection with FIG. 21 to FIG. 25.

2) Mandibular Position Remounting Function a) Structure and Function

Another embodiment of the present invention will now be described with reference to FIG. 21 to FIG. 25.

In the conventional articulators described above, once the denture models are mounted on the maxillary and mandibular model members 13 and 10, the positional relationship of the upper and lower denture models cannot be corrected. However, in actual clinical practice, in cases of temporomandibular arthrosis, or of bone fracture of the condyle part or ramus of mandible, the jaw position must often be corrected.

In the present embodiment, in such cases, it is made possible to correct the jaw position without removing the denture models on the maxillary and mandibular model members 13, 10, from the mounting plate on which they are mounted, and, if necessary, to restore the original jaw position.

For this purpose, the following four conditions should be satisfied: (1) free parallel and rotational movements of the lower denture model 90 should be possible on the frame surface of the mandibular model member 10 (clinically 7 mm movement capability in the anterior/posterior direction and 2 mm movement capability in the left-right direction is a satisfactory range); (2) the height of the incisal pin 23 should be adjustable; (3) the height of left and right condyle balls 12 should be adjustable; and (4) the distance between the left and right condyle boxes 17, 17 that receive the left and right condyle balls 12,12 should be adjustable.

Of these conditions, regarding (3), as shown in FIG. 21, the condyle balls 12 should be arranged to be freely adjustable in height by means of a screw with respect to the bases 11, and, regarding (4), the shafts 32 of the left and right condyle boxes 17 should be adjustable in position in the axial direction with respect to bearing members 13*a* at the posterior of the maxillary model member 13.

The condition (2) is as described with reference to the embodiment of FIG. 1. Regarding (1), it should be arranged that the mounting plate 96 on which the lower denture model 90 is mounted should be arranged to be capable of being moved and capable of being fixed on the plate 10*f* of the mandibular model member 10.

Figure 23:
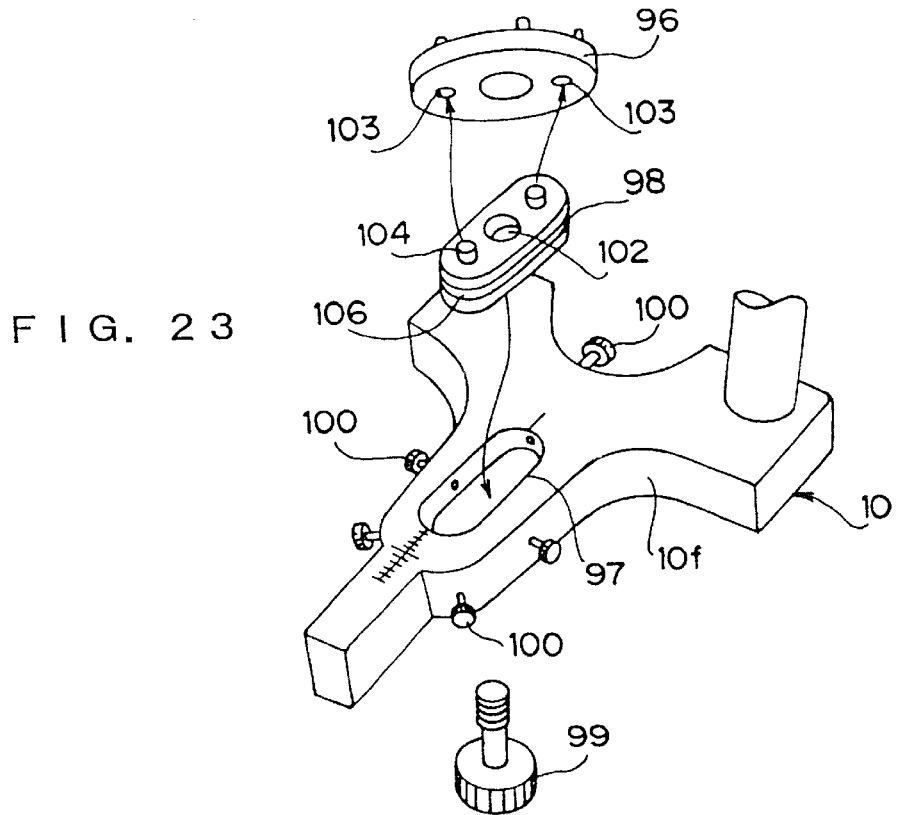
FIG. 23 is a perspective view showing details of the mandibular model member of FIG. 22.
Figure 24:
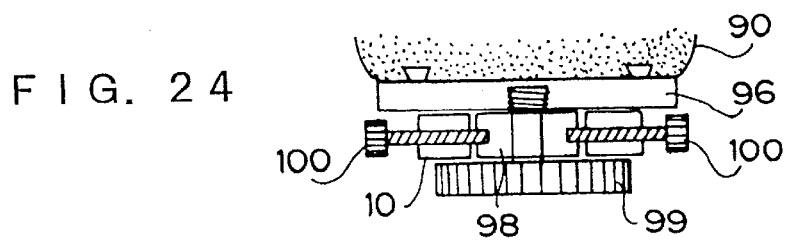
FIG. 24 is a detail cross-sectional view when the mandible denture model is mounted on the mandibular model member in connection with FIG. 22.

Specifically, as shown in FIG. 23, an oblong slot 97 is formed in the plate 10*f* of the mandibular model member 10 and an oblong pillar-shape adapter 98 is fitted into this oblong slot 97. To this adapter 98, attached is the mounting plate 96 on which the lower denture model 90 is mounted. A fixing screw 99 is screwed into the mounting plate 96 from the underneath side of the mandibular model member 10 for the fixing. Such adapters 98 may be prepared of various sizes. The position of the selected adapter 98 is adjusted by five positional location screws 100 provided on the plate 10*f* by moving the adapter in a desired direction within the oblong slot 97. Fixing is then effected as shown in FIG. 24 by screwing the fixing screw 99 into the mounting plate 96.

Figures 25A, 25B, 25C:
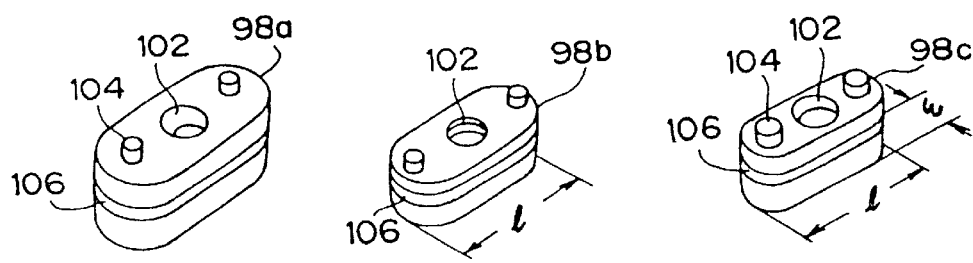
FIGS. 25a to 25c illustrate details of various adapters, each of which can be employed in FIG. 23, respectively.
Figure 26:
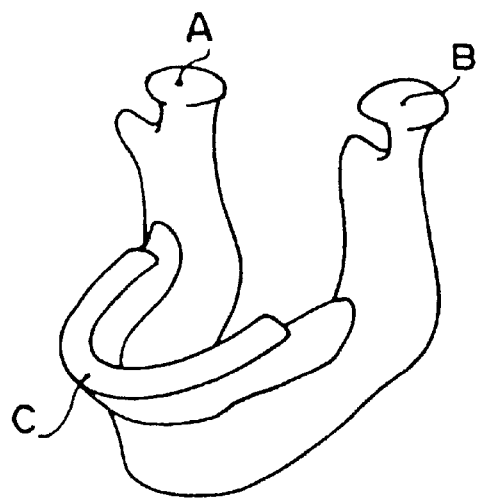
FIG. 26 illustrates the mandible of a body.
Figure 27:
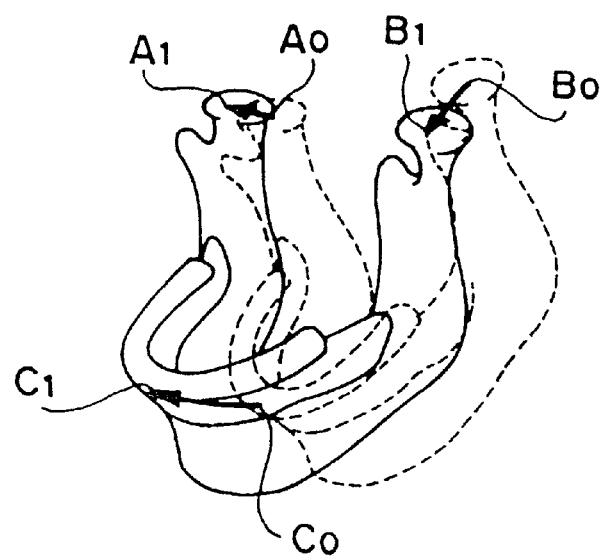
FIG. 27 illustrates the mandibular movement.
Figure 28:
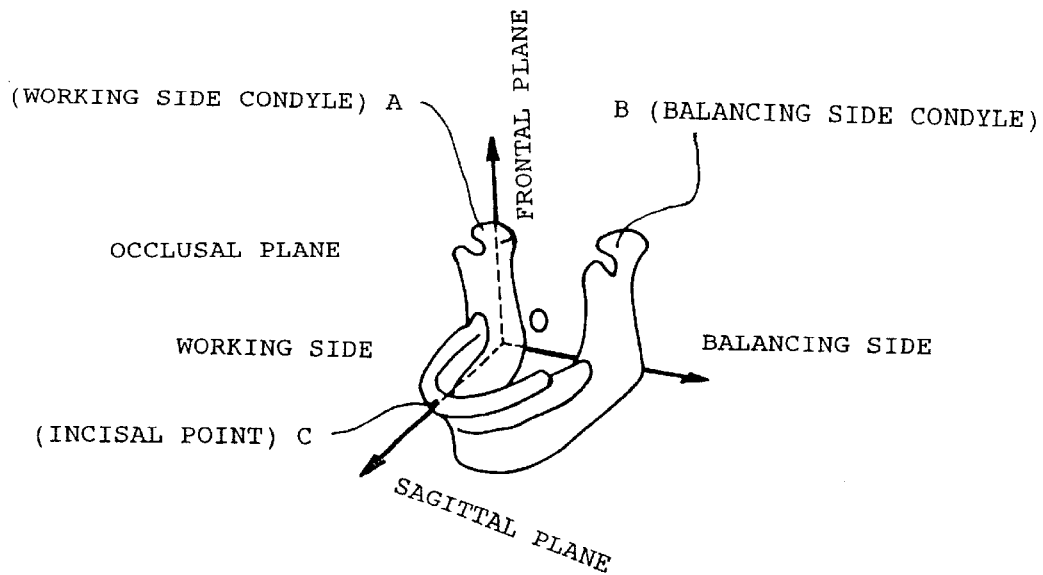
FIG. 28 is a view given in explanation of terms in dentistry.
Figure 29:
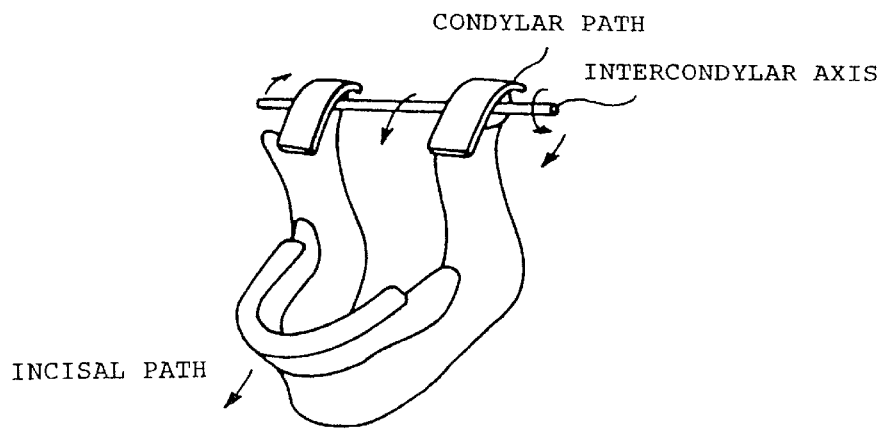
FIG. 29 depicts modeling of the mandibular movement.
Figure 30:
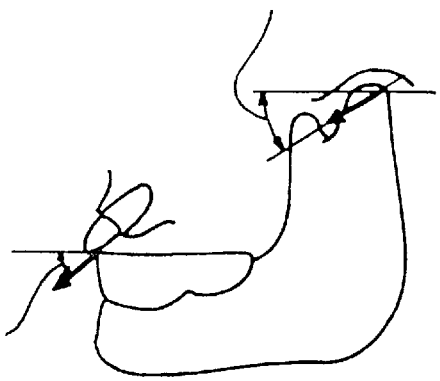
FIG. 30 depicts the direction of movement when the mandible is seen from the sagittal plane.
Figure 31:
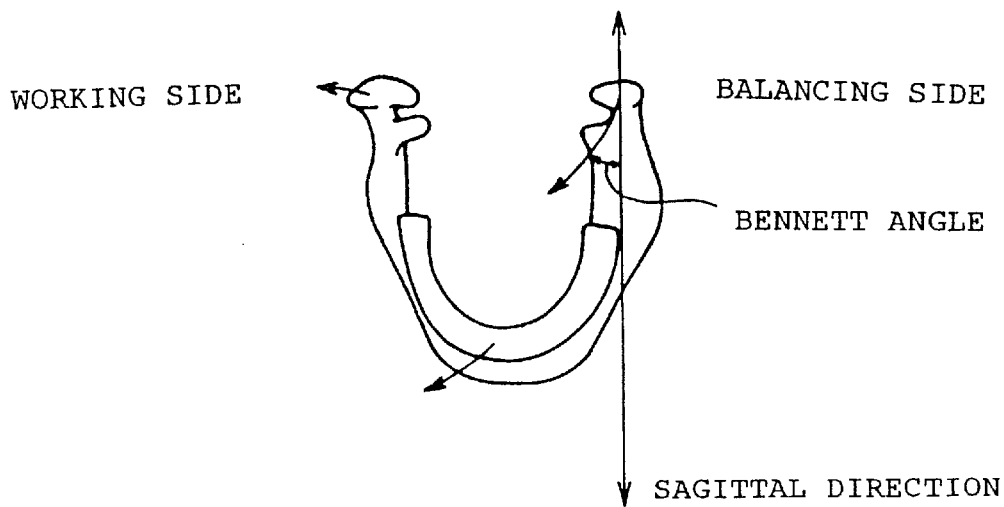
FIG. 31 illustrates the direction of movement when the mandible is seen from above the occlusal plane.

An adapter 98*a* as shown in FIG. 25*a* that makes a tight fit in the oblong slot 97 of the plate 10*f*, an adapter 98*b* as shown in FIG. 25*b* that makes a tight fit in the left/right (or width) direction, with its anterior/posterior length 1 being shorter than the anterior/posterior length of the oblong slot 97 such that it can move only in the anterior/posterior direction, and an adapter 98*c* as shown in FIG. 25*c* whose left/right width w is narrower than the width of the oblong slot 97 and whose anterior/posterior length 1 is also shorter than the oblong slot may be prepared beforehand. Positional adjustment can be performed by suitable selection of such adapters 98*a*, 98*b*, 98*c* when fixing the mounting plate 96.

Also, in the adapter 98, there are formed a hole 102 into which the fixing screw 99 is inserted, a pair of projections 104 that fit into a pair of holes 103 provided in the mounting plate 96, and a groove 106 for preventing withdrawal of the adapter 98 by engagement with the positional locating screws 100.

b) Explanation as to How Remounting can be Achieved With the Above Construction

Correction of the jaw position can be achieved by satisfying these conditions (1) to (4).

FIG. 22 shows diagrammatically how a mandibular model 90L and maxilla denture model 92U that do not match can be superimposed under the above four conditions.

Let us now assume that the triangle created by the three points (AL, BL, CL) of the mandibular model 90L and the triangle created by the three points (AU, BU, CU) of the maxilla denture model 92U are congruent. Assuming that these two triangles are not superimposed but are a little offset three-dimensionally, the way in which superimposition of the three points (AL, BL, CL) of the mandibular model 90L and the three points (AU, BU, CU) of the maxilla denture model 92U under the conditions (1) to (4) can be achieved will now be described.

(1) CU and CL can be made to coincide by sliding the mandibular model 90L over the plate 10*f* and adjusting the length of the right condyle ball 12R.

(2) With CU and CL in coincidence, BU and BL can be brought into coincidence by raising or lowering the left condyle box 17L whilst rotating the mandibular model 90L on the plate 10*f*.

(3) With BU and BL in coincidence and CU and CL in coincidence, AU and AL can be brought into coincidence by adjusting the length of the incisal pin 23.

(4) The distance between the two condyles is changed by the operations of (1) and (2). The amount of this change is very small so that clinically it can be neglected, but mechanisms for adjusting the left and right condyle boxes 17R and 17L are provided.

In this manner, superimposition of the upper and lower denture models 90 and 92 is adjustable. Therefore, even in cases of temporomandibular arthrosis, or of bone fracture of the condyle part or ramus of mandible, correction of the jaw position can be achieved without removing the upper and lower denture models 90, 92 from the mounting plate.

INDUSTRIAL APPLICABILITY

As described above, with the full reproduction articulator of the present invention, faithful and accurate reproduction of the jaw movement, particularly the chewing movement, including individual differences, can be achieved and in clinical cases in which faithful and accurate reproduction is inappropriate, ideal jaw position and jaw movement can be diagnosed, designed and implemented on this articulator.

What is claimed is:

1. A full reproduction articulator, including:
   a mandibular model member;
   a base erected on the mandibular model member;
   two condyle balls projecting from the base;

a maxillary model member that occludes the mandibular model member;

condyle boxes linked to both sides of the maxillary model member for regulating movement in an anterior/posterior direction, movement in a left/right direction and movement in a vertical direction of the maxillary model member by contacting the two condyle balls; and Bennett lift mechanisms provided on the base, one of the Bennett life mechanisms on a working side lifts the maxillary model member from the condyle ball on the working side when the maxillary model member moves in the left/right direction, independently of the condyle box on the working side.

2. The full reproduction articulator according to claim 1 wherein each of the condyle boxes includes a sagittal condylar path inclination adjustment plate of adjustable angle, a Bennett plate of adjustable angle and a rear wall plate of adjustable angle, the sagittal condylar path inclination adjustment plates regulate vertical movement during anterior/posterior movement by contacting the heads of the two condyle balls, the Bennett plate on a balancing side regulates left/right movement by contacting an inside face of the condyle ball on the balancing side, and the rear wall plate on the working side regulates anterior/posterior movement by contacting a posterior part of the condyle ball on the working side.

3. The full reproduction articulator according to claim 2 wherein the condyle boxes are respectively removably provided on the maxillary model member.

4. The full reproduction articulator according to claim 3 wherein each of the Bennett lift mechanisms includes a cam member provided on one of the base or maxillary model member and having a cam face of adjustable angle, and a pin formed on the other of the base or maxillary model member and contacting the cam face of the cam member.

5. The full reproduction articulator according to claim 4 wherein each of the Bennett lift mechanisms includes fixing means for fixing the cam member to the base or maxillary model member after angular adjustment of the cam face.

6. The full reproduction articulator according to claim 4 wherein each of the pins is arranged on the base or maxillary model member in such a way that its projecting length is adjustable.

7. The full reproduction articulator according to claim 2 wherein each of the Bennett lift mechanisms includes a cam member provided on one of the base or maxillary model member and having a cam face of adjustable angle, and a pin formed on the other of the base or maxillary model member and contacting the cam face of the cam member.

8. The full reproduction articulator according to claim 7 wherein each of the pins is arranged on the base or maxillary model member in such a way that its projecting length is adjustable.

9. The full reproduction articulator according to claim 1 wherein the condyle boxes are respectively removably provided on the maxillary model member.

10. The full reproduction articulator according to claim 9 wherein each of the Bennett lift mechanisms includes a cam member provided on one of the base or maxillary model member and having a cam face of adjustable angle, and a pin formed on the other of the base or maxillary model member and contacting the cam face of the cam member.

11. The full reproduction articulator according to claim 10 wherein each of the Bennett lift mechanisms includes fixing means for fixing the cam member to the base or maxillary model member after angular adjustment of the cam face.

12. The full reproduction articulator according to claim 10 wherein each of the pins is arranged on the base or maxillary model member in such a way that its projecting length is adjustable.

13. The full reproduction articulator according to claim 1 wherein each of the Bennett lift mechanisms includes a cam member provided on one of the base or maxillary model member and having a cam face of adjustable angle, and a pin formed on the other of the base or maxillary model member and contacting the cam face of the cam member.

14. The full reproduction articulator according to claim 13 wherein each of the Bennett lift mechanisms includes fixing means for fixing the cam member to the base or maxillary model member after angular adjustment of the cam face.

15. The full reproduction articulator according to claim 14 wherein each of the Bennett lift mechanisms includes fixing means for fixing the cam member to the base or maxillary model member after angular adjustment of the cam face.

16. The full reproduction articulator according to claim 13 wherein each of the pins is arranged on the base or maxillary model member in such a way that its projecting length is adjustable.

17. A full reproduction articulator including:

a mandibular model member;

a base erected on the mandibular model member;

two condyle balls projecting from the base and having adjustable height positions;

a maxillary model member that occludes the mandibular model member, the mandibular model member including a mandible plate, a lower denture model provided on the mandible plate and a mandibular position remounting mechanism that makes it possible to remount the lower denture model on a plane of the mandible plate; and condyle boxes linked to both sides of the maxillary model member and in contact with the two condyle balls for regulating movement of the maxillary model member in an anterior/posterior direction, left/right direction and upwards/downwards direction.

18. The full reproduction articulator according to claim 17 wherein the lower denture model is provided with a mounting plate, the mounting plate is mounted on the mandible plate such that a position of the mounting plate is remountable by means of the mandibular position remounting mechanism, and the mandibular position remounting mechanism includes a plurality of adapters that engage the mounting plate and fixing means that fix the adapter by locating it in position on the mandible plate together with the mounting plate.

19. The full reproduction articulator according to claim 18 wherein the maxillary model member has an incisal pin of adjustable height that contacts the mandible plate of the mandibular model member and sets the height of the incisal point of the upper and lower denture models.

20. The full reproduction articulator according to claim 19 further including means for variably adjusting a distance between the left and right condyle boxes, and wherein on correction of a jaw position, the lower denture model is moved on a mandible plate surface, the height of the incisal pin is adjusted and the height of the condyle balls is adjusted.

* * * * *